(12) United States Patent
Belldegrun et al.

(10) Patent No.: US 11,197,917 B2
(45) Date of Patent: Dec. 14, 2021

(54) FORMULATIONS FOR NUTRITIONAL SUPPORT IN SUBJECTS IN NEED THEREOF

(71) Applicant: ByHeart, Inc., New York, NY (US)

(72) Inventors: Ron Belldegrun, New York, NY (US); Mia Funt, New York, NY (US)

(73) Assignee: ByHeart, Inc., New York, NY (US)

( * ) Notice: Subject to any disclaimer, the term of this patent is extended or adjusted under 35 U.S.C. 154(b) by 516 days.

(21) Appl. No.: 15/829,703

(22) Filed: Dec. 1, 2017

(65) Prior Publication Data

US 2019/0167766 A1    Jun. 6, 2019

(51) Int. Cl.
| | |
|---|---|
| A61K 38/40 | (2006.01) |
| A61K 38/01 | (2006.01) |
| A61K 38/38 | (2006.01) |
| A61K 38/19 | (2006.01) |
| A61K 9/00 | (2006.01) |
| A23L 33/00 | (2016.01) |
| A23L 33/19 | (2016.01) |
| A23L 33/115 | (2016.01) |
| A23L 33/125 | (2016.01) |

(52) U.S. Cl.
CPC ............ *A61K 38/40* (2013.01); *A23L 33/115* (2016.08); *A23L 33/125* (2016.08); *A23L 33/19* (2016.08); *A23L 33/40* (2016.08); *A61K 9/0095* (2013.01); *A61K 38/018* (2013.01); *A61K 38/19* (2013.01); *A61K 38/38* (2013.01); *A23V 2002/00* (2013.01)

(58) Field of Classification Search
CPC ........ A23L 33/19; A23L 33/40; A23L 33/115; A23L 33/125; A61K 38/018; A61K 38/19; A61K 38/38; A61K 38/40; A61K 9/0095; A23V 2002/00; A61P 1/14
See application file for complete search history.

(56) References Cited

U.S. PATENT DOCUMENTS

| | | |
|---|---|---|
| 3,978,234 A | 8/1976 | Bosund et al. |
| 4,107,334 A | 8/1978 | Jolly |
| 4,216,236 A | 8/1980 | Mueller et al. |
| 4,293,583 A | 10/1981 | Farr et al. |
| 4,716,045 A | 12/1987 | Prella |
| 4,748,034 A | 5/1988 | de Rham |
| 5,039,532 A | 8/1991 | Jost et al. |
| 5,080,921 A | 1/1992 | Reimer |
| 5,635,199 A | 6/1997 | Trimbo et al. |
| 5,714,182 A | 2/1998 | Bisson et al. |
| 5,766,621 A | 6/1998 | Trimbo et al. |
| 5,795,611 A | 8/1998 | Slattery |
| 5,891,698 A | 4/1999 | Prieto et al. |
| 5,921,955 A | 7/1999 | Mazer et al. |
| 6,106,874 A | 8/2000 | Liebrecht et al. |
| 6,146,670 A | 11/2000 | Prieto et al. |
| 6,171,621 B1 | 1/2001 | Braun et al. |
| 6,190,724 B1 | 2/2001 | Sawatzki et al. |
| 6,200,950 B1 | 3/2001 | Mark et al. |
| 6,207,293 B1 | 3/2001 | Ragland et al. |
| 6,228,886 B1 | 5/2001 | Anderson et al. |
| 6,270,827 B1 | 8/2001 | Gaull |
| 6,365,218 B1 | 4/2002 | Borschel et al. |
| 6,372,782 B1 | 4/2002 | Patel et al. |
| 6,495,170 B1 | 12/2002 | Smit et al. |
| 6,589,576 B2 | 7/2003 | Borschel et al. |
| 6,592,863 B2 | 7/2003 | Fuchs et al. |
| 6,613,367 B1 | 9/2003 | Wells et al. |
| 6,716,466 B2 | 4/2004 | Kuslys et al. |
| 6,733,770 B1 | 5/2004 | Garcia-Rodenas et al. |
| 6,737,076 B2 | 5/2004 | Fritsche et al. |
| 6,811,804 B2 | 11/2004 | Patel et al. |
| 6,849,595 B2 | 2/2005 | Mark et al. |
| 6,867,178 B1 | 3/2005 | Mark et al. |
| 6,887,850 B2 | 5/2005 | Fuchs et al. |
| 6,913,778 B2 | 7/2005 | Kuhlman et al. |
| 7,070,825 B2 | 7/2006 | Ndife et al. |
| 7,247,320 B2 | 7/2007 | Jost |
| 7,375,089 B2 | 5/2008 | Verlaan et al. |
| 7,572,474 B2 | 8/2009 | Petschow et al. |
| 7,618,669 B2 | 11/2009 | Rangavajla et al. |
| 7,651,716 B2 | 1/2010 | Davis et al. |
| 7,666,830 B2 | 2/2010 | Garcia-Rodenas et al. |
| 7,776,332 B1 | 8/2010 | Kuslys et al. |
| 8,003,600 B2 | 8/2011 | Hageman |

(Continued)

FOREIGN PATENT DOCUMENTS

| | | | |
|---|---|---|---|
| CA | 2 922 242 A1 | | 3/2015 |
| CN | 102524422 A | | 7/2012 |
| CN | 104430899 A | * | 3/2015 |
| CN | 104489101 A | | 4/2015 |
| CN | 104982533 A | | 10/2015 |

(Continued)

OTHER PUBLICATIONS

Google translation of CN104430899A, accessed on May 5, 2020.*
Donald K. Layman, Applications for a-lactalbumin in human nutrition, Nutrition ReviewsVR vol. 76(6):444-460, 2018.*
Demmelmair H., et al., "Benefits of Lactoferrin, Osteopontin and Milk Fat Globule Membranes for Infants", Nutrients, 2017, pp. 1-22, vol. 9, issue 8.
International Search Report and Written Opinion of the International Searching Authority for International Application No. PCT/US2018/063427, dated Feb. 27, 2019.

(Continued)

*Primary Examiner* — James H Alstrum-Acevedo
*Assistant Examiner* — Erinne R Dabkowski
(74) *Attorney, Agent, or Firm* — Jon E. Gordon; David Zwally; Haug Partners LLP

(57) ABSTRACT

Formulations having a protein component, in which the protein contains one or more digestion-aiding proteins, and/or one or more immunoprotective proteins. The formulations may also contain a fat component, a carbohydrate component, and vitamins and minerals. These formulations can be used to provide nutritional support to a subject, either as dietary supplements or as a primary source of nutrition, such as for an infant formula.

4 Claims, No Drawings

(56) References Cited

U.S. PATENT DOCUMENTS

| | | |
|---|---|---|
| 8,021,708 B2 | 9/2011 | Petschow et al. |
| 8,057,839 B2 | 11/2011 | Bovetto et al. |
| 8,075,934 B2 | 12/2011 | Banavara et al. |
| 8,114,441 B2 | 2/2012 | Boehm et al. |
| 8,124,585 B2 | 2/2012 | Hageman et al. |
| 8,147,894 B2 | 4/2012 | Euber et al. |
| 8,277,863 B2 | 10/2012 | Petschow et al. |
| 8,287,931 B2 | 10/2012 | Rosales et al. |
| 8,293,264 B2 | 10/2012 | Rosales et al. |
| 8,329,190 B2 | 12/2012 | Vidal et al. |
| 8,350,006 B2 | 1/2013 | Rai et al. |
| 8,377,430 B2 | 2/2013 | Donnet-Hughes et al. |
| 8,377,496 B2 | 2/2013 | Clinger et al. |
| 8,388,949 B2 | 3/2013 | Hageman |
| 8,409,651 B2 | 4/2013 | Sliwinski et al. |
| 8,425,955 B2 | 4/2013 | Wittke |
| 8,445,429 B2 | 5/2013 | Faure et al. |
| 8,450,347 B2 | 5/2013 | Hageman et al. |
| 8,501,676 B2 | 8/2013 | Hageman |
| 8,524,658 B2 * | 9/2013 | Wang ............... A61P 27/02 514/2.5 |
| 8,557,320 B2 | 10/2013 | Petschow et al. |
| 8,580,316 B2 | 11/2013 | Boehm et al. |
| 8,591,981 B2 | 11/2013 | Sprenger et al. |
| 8,618,047 B2 | 12/2013 | Hofman et al. |
| 8,648,036 B2 | 2/2014 | Wittke et al. |
| 8,703,725 B2 | 4/2014 | Troup et al. |
| 8,722,384 B2 | 5/2014 | Knutzon et al. |
| 8,754,064 B2 | 6/2014 | M'Rabet et al. |
| 8,815,797 B2 | 8/2014 | Minor et al. |
| 8,846,612 B2 | 9/2014 | Aprikian et al. |
| 8,846,759 B2 | 9/2014 | Luiking et al. |
| 8,853,148 B2 | 10/2014 | Miller et al. |
| 8,857,317 B2 | 10/2014 | Manser et al. |
| 8,865,649 B2 | 10/2014 | Hageman |
| 8,916,217 B2 | 12/2014 | Johns et al. |
| 8,968,722 B2 | 3/2015 | Wittke |
| 8,986,769 B2 | 3/2015 | Gonzalez et al. |
| 8,999,423 B2 | 4/2015 | Sliwinski et al. |
| 8,999,924 B2 | 4/2015 | Sliwinski et al. |
| 9,049,882 B2 | 6/2015 | Van Der Zande et al. |
| 9,060,996 B2 | 6/2015 | Knippels et al. |
| 9,066,537 B2 | 6/2015 | Hofman et al. |
| 9,072,314 B2 | 7/2015 | Jouni et al. |
| 9,078,466 B2 | 7/2015 | Boehm et al. |
| 9,078,847 B2 | 7/2015 | Lai |
| 9,084,804 B2 | 7/2015 | Groenendijk et al. |
| 9,089,157 B2 | 7/2015 | Wittke et al. |
| 9,095,570 B2 | 8/2015 | Faure et al. |
| 9,107,867 B2 | 8/2015 | Zanghi et al. |
| 9,119,838 B2 | 9/2015 | Knippels et al. |
| 9,131,721 B2 | 9/2015 | Rochat et al. |
| 9,179,702 B2 | 11/2015 | DeWille et al. |
| 9,198,445 B2 | 12/2015 | Schmitt et al. |
| 9,226,914 B2 | 1/2016 | Kuang et al. |
| 9,226,945 B2 | 1/2016 | Mercenier et al. |
| 9,241,508 B2 | 1/2016 | Kensler et al. |
| 9,241,923 B2 | 1/2016 | Kuang et al. |
| 9,301,966 B2 | 4/2016 | Berg |
| 9,345,256 B2 | 5/2016 | Sliwinski et al. |
| 9,351,506 B2 | 5/2016 | Bontemps |
| 9,351,978 B2 | 5/2016 | Kuang et al. |
| 9,420,816 B2 | 8/2016 | Minor et al. |
| 9,439,448 B2 | 9/2016 | Rosales et al. |
| 9,474,298 B2 | 10/2016 | Vanderhoof et al. |
| 9,486,003 B2 | 11/2016 | Bolster et al. |
| 9,492,502 B2 | 11/2016 | Van den Braak et al. |
| 9,497,983 B2 | 11/2016 | Minor et al. |
| 9,539,278 B2 | 1/2017 | Hageman |
| 9,549,569 B2 | 1/2017 | Roessle |
| 9,555,103 B2 | 1/2017 | Knippels et al. |
| 9,579,347 B2 | 2/2017 | Pereira et al. |
| 9,585,900 B2 | 3/2017 | De Wilde et al. |
| 9,603,888 B2 | 3/2017 | Georgi et al. |
| 9,609,888 B2 | 4/2017 | Berg et al. |
| 9,642,390 B2 | 5/2017 | van Norren et al. |
| 9,649,380 B2 | 5/2017 | Longoni et al. |
| 9,661,868 B2 | 5/2017 | Banavara et al. |
| 9,675,097 B2 | 6/2017 | Patel et al. |
| 9,682,119 B2 | 6/2017 | Hofman et al. |
| 9,757,345 B2 | 9/2017 | Walton et al. |
| 9,770,460 B2 | 9/2017 | Knippels et al. |
| 9,827,216 B2 | 11/2017 | Schiffrin et al. |
| 9,844,227 B2 | 12/2017 | Vurma et al. |
| 9,844,531 B2 | 12/2017 | Garvey et al. |
| 9,867,796 B2 | 1/2018 | Van Norren et al. |
| 9,872,888 B2 | 1/2018 | De Kort et al. |
| 2003/0124237 A1 | 7/2003 | Kuhlman et al. |
| 2005/0142249 A1 | 6/2005 | Davis et al. |
| 2006/0073186 A1 | 8/2006 | Kume et al. |
| 2006/0171992 A1 | 8/2006 | Gerhardt et al. |
| 2006/0286210 A1 | 12/2006 | Rangavajla et al. |
| 2007/0166411 A1 | 7/2007 | Anthony et al. |
| 2008/0138435 A1 | 6/2008 | Van Den Berg et al. |
| 2009/0087540 A1 | 4/2009 | Haschke et al. |
| 2009/0092590 A1 | 4/2009 | Rangavajla et al. |
| 2009/0118228 A1 | 5/2009 | Jouni et al. |
| 2009/0142375 A1 | 6/2009 | Vidal et al. |
| 2009/0203592 A1 | 8/2009 | Beermann et al. |
| 2010/0047393 A1 | 2/2010 | Glas et al. |
| 2011/0021428 A1 | 1/2011 | Mercenier et al. |
| 2011/0028389 A1 | 2/2011 | Steenhout |
| 2011/0165237 A1 | 7/2011 | Mark et al. |
| 2011/0236500 A1 | 9/2011 | Van Den Berg et al. |
| 2011/0250317 A1 | 10/2011 | Secretin |
| 2011/0256260 A2 | 10/2011 | Knutzon et al. |
| 2011/0263505 A1 | 10/2011 | Henle et al. |
| 2012/0015077 A1 | 1/2012 | Secretin |
| 2012/0135103 A1 | 5/2012 | Walsh et al. |
| 2012/0171231 A1 | 7/2012 | Wittke et al. |
| 2012/0184484 A1 | 7/2012 | Wang et al. |
| 2012/0189598 A1 | 7/2012 | Mercenier et al. |
| 2012/0245122 A1 | 9/2012 | Jouni et al. |
| 2012/0321600 A1 | 12/2012 | Benyacoub et al. |
| 2013/0078362 A1 | 3/2013 | DeWille et al. |
| 2013/0089572 A1 | 4/2013 | Vanderhoof et al. |
| 2013/0266684 A1 | 10/2013 | Fitzgerald et al. |
| 2014/0037602 A1 | 2/2014 | Bolster et al. |
| 2014/0037788 A1 | 2/2014 | Haschke et al. |
| 2014/0044830 A1 | 2/2014 | Mace et al. |
| 2014/0199265 A1 | 7/2014 | Kuang et al. |
| 2014/0242216 A1 | 8/2014 | Ao et al. |
| 2014/0255365 A1 | 9/2014 | Gonzalez et al. |
| 2014/0255539 A1 | 9/2014 | Banavara et al. |
| 2014/0271978 A1 | 9/2014 | Wittke et al. |
| 2014/0308393 A1 | 10/2014 | Marriage et al. |
| 2014/0323574 A1 | 10/2014 | Yao et al. |
| 2014/0328970 A1 | 11/2014 | Alvey et al. |
| 2014/0335129 A1 | 11/2014 | Knippels et al. |
| 2015/0110919 A1 | 4/2015 | Johns et al. |
| 2015/0118351 A1 | 4/2015 | Haschke et al. |
| 2015/0119322 A1 | 4/2015 | Chichlowski et al. |
| 2015/0125570 A1 | 5/2015 | Wittke |
| 2015/0157048 A1 | 6/2015 | Gaygadzhiev |
| 2015/0157697 A1 | 6/2015 | Wang |
| 2015/0189905 A1 | 7/2015 | Banavara et al. |
| 2015/0231213 A1 | 8/2015 | Chichlowski et al. |
| 2015/0246090 A1 | 9/2015 | Knippels et al. |
| 2015/0246100 A1 | 9/2015 | Donovan et al. |
| 2015/0290260 A1 | 10/2015 | Chichlowski et al. |
| 2015/0290261 A1 | 10/2015 | Chichlowski et al. |
| 2015/0305383 A1 | 10/2015 | Georgi et al. |
| 2015/0305385 A1 | 10/2015 | Chichlowski et al. |
| 2016/0015068 A1 | 1/2016 | Ao et al. |
| 2016/0029682 A1 | 2/2016 | Solorio et al. |
| 2016/0050960 A1 | 2/2016 | Van Den Braak et al. |
| 2016/0082078 A1 | 3/2016 | Molenaar |
| 2016/0166638 A1 | 6/2016 | Kastenmayer et al. |
| 2016/0174588 A1 | 6/2016 | Mateus et al. |
| 2016/0193302 A1 | 7/2016 | Wang et al. |
| 2016/0213041 A1 | 7/2016 | Johns et al. |
| 2016/0302464 A1 | 10/2016 | Egli et al. |
| 2016/0353774 A1 | 12/2016 | Gonzalez |
| 2016/0354323 A1 | 12/2016 | Kuang et al. |

(56) References Cited

U.S. PATENT DOCUMENTS

| | | |
|---|---|---|
| 2017/0006897 A1 | 1/2017 | Ao et al. |
| 2017/0007629 A1 | 1/2017 | Kuang et al. |
| 2017/0020180 A1 | 1/2017 | Affolter et al. |
| 2017/0027214 A1 | 2/2017 | Affolter et al. |
| 2017/0094991 A1 | 4/2017 | Banavara et al. |
| 2017/0128500 A1 | 5/2017 | Zhong et al. |
| 2017/0128548 A1 | 5/2017 | Wang |
| 2017/0182132 A1 | 6/2017 | Wittke et al. |
| 2017/0209472 A1 | 7/2017 | Jeurink et al. |
| 2017/0216373 A1 | 8/2017 | Longoni et al. |
| 2017/0273997 A1 | 9/2017 | Sakwinska et al. |
| 2017/0296563 A1 | 10/2017 | Potappel-Van 'T Land et al. |
| 2017/0367395 A1 | 12/2017 | Kline et al. |

FOREIGN PATENT DOCUMENTS

| | | | | |
|---|---|---|---|---|
| CN | 107156302 A | 9/2017 | | |
| WO | WO-2014099134 A1 * | 6/2014 | ............. | A23L 33/40 |
| WO | 2018009647 A1 | 1/2018 | | |

OTHER PUBLICATIONS

Davis AM., et al., "a-Lactalbumin-Rich Infant Formula Fed to Healthy Term Infants in a Multicenter Study: Plasma Essential Amino Acids and Gastrointestinal Tolerance", European Journal of Clinical Nutrition, 2008, pp. 1294-1301, vol. 62.

Lacprodan ALPHA-10, Arla Food Ingredients, Product Sheet 0063, dated Jul. 29, 2014, pp. 1-3.

Lacprodan ALPHA-20, Arla Food Ingredients, Product Information 1282, dated Mar. 2, 2015, pp. 1-3.

Ashley C., et al., "Growth and Tolerance of Infants Fed Formula Supplemented with Polydextrose (PDX) and/or Galactooligosaccharides (GOS): Double-Blind, Randomized, Controlled Trial", Nutrition Journal, 2012, pp. 1-10, vol. 11, No. 38.

Vandenplas Y., et al., "Prebiotics in Infant Formula", Gut Microbes, 2014, pp. 681-687, vol. 5, No. 6.

Do Carmo, MMR., et al., "Polydextrose: Physiological Function, and Effects on Health", Nutrients, 2016, pp. 1-13, vol. 8, No. 553.

Silanikove N., et. al., "The Interrelationships between Lactose Intolerance and the Modern Dairy Industry: Global Perspectives in Evolutional and Historical Backgrounds", Nutrients, 2015, pp. 7312-7331, vol. 7.

Alothman M., et al., "The 'Grass-Fed' Milk Story: Understanding the Impact of Pasture Feeding on the Composition and Quality of Bovine Milk", Foods, 2019, pp. 1-24, vol. 8, No. 350.

Mansson HL., "Fatty Acids in Bovine Milk Fat", Food and Nutrition Research, 2008, DOI: 10.3402/fnr.v52i0.1821.

U.S. Appl. No. 16/428,589, filed May 31, 2019, 2019/0388518, Pending.

Database GNPD [Online] MINTEL; Oct. 1, 2015 (Oct. 1, 2015), anonymous: "Stage 1 Baby Formula," XP055820481, Database accession No. 3414417.

Database GNPD [Online] MINTEL; Oct. 20, 2017 (Oct. 20, 2017), anonymous: "Stage 1 Infant Formula," XP055820477, Database accession No. 5175659.

Supplementary European Search Report dated Jul. 15, 2021 in corresponding European Application No. EP 18 88 3382.

* cited by examiner

FORMULATIONS FOR NUTRITIONAL SUPPORT IN SUBJECTS IN NEED THEREOF

FIELD OF THE DISCLOSURE

The disclosure relates to formulations that can provide nutritional support to a subject, for example, as a dietary supplement or as a primary source of nutrition. In some applications, the formulation may be used in an exempt infant formula, infant formula, or medical food.

BACKGROUND

While it is generally recommended that infants are fed breast milk, in many cases breast feeding is not feasible or adequate, or the parent(s) choose not to breast feed. To this end, infant formulas have been developed with the primary objective of providing the nutrition that infants would otherwise receive from breast milk.

However, many infant formulas on the market are not formulated to provide the full nutritional and health benefits seen with breast milk, which is primarily due to the proteins included in these formulas. For example, research in this area has shown certain intact proteins—and their peptides that are naturally produced through the digestive process—provide bioactivity that may be important for the development of a baby's immune system, and support for anti-viral, antibacterial, immunomodulatory and anti-inflammatory effects. These proteins are often absent or in insufficient quantities in current infant formulas. Moreover, cow-based infant formulas are often missing proteases that help break down proteins and aid in digestion, which can make infant formulas difficult to digest and tolerate.

Some infant formulas on the market today are formulated to address either digestion comfort or immunity, but not both. The products formulated for digestive comfort are typically 100% partially hydrolyzed from whey protein, which may improve tolerability. But these formulas are made up of nearly all protein hydrolysates, and may neglect important bioactive peptides that are a bi-product of digestion of intact protein. These 100% hydrolyzed formulas also lack important intact bioactive proteins present in both bovine milk and human milk, such as lactoferrin and osteopontin, which have important immunity-protective properties. On the other hand, the few infant formulas that incorporate any bioactive protein supporting immunity are typically made up of only intact proteins and are not specifically formulated for easy digestion such as by including partially hydrolyzed proteins. In addition, many current infant formulas do not limit the bovine-based proteins, such as beta-lactaglobulin, which are not in human milk and which may be a source of the digestive sensitivity to the formula.

Thus, there is a continuing need to develop infant formulas that are easy to digest and that provide the nutritional and bioactive benefits of breast milk.

SUMMARY OF INVENTION

One aspect of the invention relates to a formulation for oral administration comprising a protein component, in which the protein component comprises whey protein hydrolysate (WPH) protein and alpha-lactalbumin.

In some embodiments, the WPH protein and the alpha-lactalbumin are present in a ratio of about 4:1 to about 1:1, or about 7:2 to about 5:4 by weight.

In certain embodiments, the WPH protein and the alpha-lactalbumin comprise about 15% to about 80%, or about 30% to about 70%, by weight of the protein component. In certain embodiments, the WPH protein and the alpha-lactalbumin comprise about 40%, or about 44%, or about 49%, or about 53%, or about 59%, or about 63% by weight of the protein component.

In some embodiments, the WPH protein comprises about 10% to about 55%, or about 20% to about 50%, by weight of the protein component. In certain embodiments, the WPH protein comprises about 26%, about 35%, or about 45% by weight of the protein component.

In some embodiments, the alpha-lactalbumin comprises about 5% to about 25%, or about 10% to about 20%, by weight of the protein component. In certain embodiments, the alpha-lactalbumin comprises about 14% or about 18% by weight of the protein component.

In certain embodiments, the WPH protein comprises about 26% or about 35% or about 45% by weight of the protein component, and the alpha-lactalbumin comprises about 14% or about 18% by weight of the protein component.

The protein component may further comprise one or more immunoprotective proteins. In some embodiments, the one or more immunoprotective proteins are selected from the group consisting of lactoferrin, osteopontin, K-casein, haptocorrin, lysozyme, secretory IgA, and bile-salt stimulated lipase. In some embodiments, the one or more immunoprotective proteins comprise lactoferrin, osteopontin, or both lactoferrin and osteopontin.

In some embodiments, the lactoferrin comprises about 4% to about 10%, or about 6% to about 7%, by weight of the protein component. In certain embodiments, the lactoferrin comprises about 6% or about 7% by weight of the protein component.

In some embodiments, the osteopontin comprises about 0.1% to about 2%, or about 0.5% to about 1.5%, by weight of the protein component. In certain embodiments, the osteopontin comprises about 1% by weight of the protein component.

In some embodiments, the protein component comprises about 5% to about 20%, or about 8% to about 16%, by weight of the formulation. In certain embodiments, the protein component comprises about 10% or about 15% by weight of the formulation.

The formulations may further comprise a fat component, a milk component, a carbohydrate component.

In some embodiments, the fat component comprises innate milk fat globule membrane (MFGM), added MFGM, phospholipids, cholesterol, oil, non-hexane extracted docosahexaenoic acid (DHA), hexane extracted arachidonic acid (AA), non-hexane extracted AA, or a combination thereof. In certain embodiments, the oil comprises vegetable oil, soy oil, palm oil, or a combination thereof.

In some embodiments, the milk component comprises milk from a non-human source, such as bovine milk. In certain embodiments, the milk comprises whole milk. In some embodiments, the milk is in an amount to provide about 8% to about 40%, or about 12% to about 30%, by weight of the protein component. In certain embodiments, the milk is in an amount to provide about 16%, or about 18%, or about 25%, by weight of the protein component.

In some embodiments, the carbohydrate component comprises lactose, galactooligosaccharide (GOS), fructooligosaccharide (FOS), inulin, corn syrup solids, maltodextrin, or a combination thereof.

In some embodiments, the formulation is in a powder form.

Another aspect of the present invention relates to a formulation for oral administration comprising a protein component that comprises lactoferrin and osteopontin, in which the lactoferrin and osteopontin comprise about 5% to about 10% by weight of the protein component, and the formulation further comprises a milk component comprising milk from a non-human source.

In some embodiments, the lactoferrin and osteopontin are present in a ratio of about 10:1 to about 5:1, or about 9:1 to about 6:1, by weight.

In some embodiments, the lactoferrin and osteopontin comprise about 4% to about 12%, or about 6% to about 9%, by weight of the protein component. In certain embodiments, the lactoferrin and osteopontin comprise about 7% to about 8% by weight of the protein component.

In some embodiments, the lactoferrin comprises about 4% to about 10%, or about 6% to about 7%, by weight of the protein component. In certain embodiments, the lactoferrin comprises about 6% or about 7% by weight of the protein component.

In some embodiments, the osteopontin comprises about 0.1% to about 2%, or about 0.5% to about 1.5%, by weight of the protein component. In certain embodiments, the osteopontin comprises about 1% by weight of the protein component.

In certain embodiments, the lactoferrin comprises about 6% or about 7% by weight of the protein component, and the osteopontin comprises about 1% by weight of the protein component.

In embodiments of the invention, the protein component further comprises one or more digestion-aiding proteins. In certain embodiments, the one or more digestion-aiding proteins comprise WPH protein, alpha-lactalbumin, or both WPH protein and alpha-lactalbumin.

In some embodiments, the WPH protein comprises about 10% to about 55%, or about 20% to about 50%, by weight of the protein component. In certain embodiments, the WPH protein comprises about 26%, or about 35%, or about 45% by weight of the protein component.

In some embodiments, the alpha-lactalbumin comprises about 5% to about 25%, or about 10% to about 20%, by weight of the protein component. In certain embodiments, the alpha-lactalbumin comprises about 14% or about 18% by weight of the protein component.

In some embodiments, the protein component comprises about 5% to about 20%, or about 8% to about 16%, by weight of the formulation. In certain embodiments, the protein component comprises about 10% or about 15% by weight of the formulation.

The formulations may further comprise a fat component, a milk component, a carbohydrate component, or a combination thereof.

In some embodiments, the fat component comprises innate MFGM, added MFGM, phospholipids, cholesterol, oil, non-hexane extracted DHA, hexane extracted AA, non-hexane extracted AA, or a combination thereof. In certain embodiments, the oil comprises vegetable oil, soy oil, palm oil, or a combination thereof.

In some embodiments, the milk component comprises milk from a non-human source, such as bovine milk. In certain embodiments, the milk comprises whole milk. In some embodiments, the milk is in an amount to provide about 8% to about 40%, or about 12% to about 30%, by weight of the protein component. In certain embodiments, the milk is in an amount to provide about 16%, or about 18%, or about 25% by weight of the protein component.

In some embodiments, the carbohydrate component comprises lactose, GOS, FOS, inulin, corn syrup solids, maltodextrin, or a combination thereof.

In some embodiments, the formulation is in a powder form.

An aspect of the present invention relates to a formulation for oral administration comprising a protein component, in which the protein component comprises: (a) one or more digestion-aiding proteins, selected from the group consisting of WPH protein, alpha-lactalbumin, and κ-casein; and (b) one or more immunoprotective proteins, selected from the group consisting of lactoferrin, osteopontin, κ-casein, haptocorrin, lysozyme, secretory IgA, and bile-salt stimulated lipase; in which the one or more digestion-aiding proteins and the one or more immunoprotective proteins comprise about 5% to and about 95% by weight of the protein component; and the formulation further comprises a milk component comprising milk from a non-human source.

In some embodiments, the one or more digestion-aiding proteins comprise WPH protein, and the one or more immunoprotective proteins comprise lactoferrin. In certain embodiments, the WPH protein and lactoferrin are present in a ratio of about 9:1 to about 1:1, or about 8:1 to about 3:1, by weight.

In some embodiments, the WPH protein comprises about 10% to about 55%, or about 20% to about 50%, by weight of the protein component. In certain embodiments, the WPH protein comprises about 26%, or about 35%, or about 45% by weight of the protein component.

In some embodiments, the lactoferrin comprises about 4% to about 10%, or about 6% to about 7%, by weight of the protein component. In certain embodiments, the lactoferrin comprises about 6% or about 7% by weight of the protein component.

In some embodiments, the one or more digestion-aiding proteins comprise WPH protein, and the one or more immunoprotective proteins comprise osteopontin. In certain embodiments, the WPH protein and osteopontin are present in a ratio of about 60:1 to about 10:1, or about 50:1 to about 25:1, by weight.

In some embodiments, the WPH protein comprises about 10% to about 55%, or about 20% to about 50%, by weight of the protein component. In certain embodiments, the WPH protein comprises about 26%, or about 35%, or about 45% by weight of the protein component.

In some embodiments, the osteopontin comprises about 0.1% to about 2%, or about 0.5% to about 1.5%, by weight of the protein component. In certain embodiments, the osteopontin comprises about 1% by weight of the protein component.

In some embodiments, the one or more digestion-aiding proteins comprise alpha-lactalbumin, and the one or more immunoprotective proteins comprise lactoferrin. In certain embodiments, the alpha-lactalbumin and lactoferrin are present in a ratio of about 4:1 to about 1:1, or about 3:1 to about 2:1, by weight.

In some embodiments, the alpha-lactalbumin comprises about 5% to about 25%, or about 10% to about 20%, by weight of the protein component. In certain embodiments, the alpha-lactalbumin comprises about 14% or about 18% by weight of the protein component.

In some embodiments, the lactoferrin comprises about 4% to about 10%, or about 6% to about 7%, by weight of the protein component. In certain embodiments, the lactoferrin comprises about 6% or about 7% by weight of the protein component.

In some embodiments, the one or more digestion-aiding proteins comprise alpha-lactalbumin, and the one or more immunoprotective proteins comprise osteopontin. In certain embodiments, the alpha-lactalbumin and osteopontin are present in a ratio of about 25:1 to about 10:1, or about 20:1 to about 15:1, by weight.

In some embodiments, the alpha-lactalbumin comprises about 5% to about 25%, or about 10% to about 20%, by weight of the protein component. In certain embodiments, the alpha-lactalbumin comprises about 14% or about 18% by weight of the protein component.

In some embodiments, the osteopontin comprises about 0.1% to about 2%, or about 0.5% to about 1.5%, by weight of the protein component. In certain embodiments, the osteopontin comprises about 1% by weight of the protein component.

In some embodiments, the protein component comprises about 5% to about 20%, or about 8% to about 16%, by weight of the formulation. In certain embodiments, the protein component comprises about 10% or about 15% by weight of the formulation.

The formulations may further comprise a fat component, a milk component, a carbohydrate component, or a combination thereof.

In some embodiments, the fat component comprises innate MFGM, added MFGM, phospholipids, cholesterol, oil, non-hexane extracted DHA, hexane extracted AA, non-hexane extracted AA, or a combination thereof. In certain embodiments, the oil comprises vegetable oil, soy oil, palm oil, or a combination thereof.

In some embodiments, the milk component comprises milk from a non-human source, such as bovine milk. In certain embodiments, the milk comprises whole milk. In some embodiments, the milk is in an amount to provide about 8% to about 40%, or about 12% to about 30%, by weight of the protein component. In certain embodiments, the milk is in an amount to provide about 16%, or about 18%, or about 25%, by weight of the protein component.

In some embodiments, the carbohydrate component comprises lactose, GOS, FOS, inulin, corn syrup solids, maltodextrin, or a combination thereof.

In some embodiments, the formulation is in a powder form.

A further aspect of the present invention relates to a formulation for oral administration comprising a protein component and a fat component, in which the protein component comprises osteopontin, and the fat component comprises MFGM, and in which the formulation comprises a milk component comprising milk from a non-human source.

In some embodiments, the osteopontin comprises about 0.1% to about 2%, or about 0.5% to about 1.5%, by weight of the protein component. In certain embodiments, the osteopontin comprises about 1% by weight of the protein component.

In some embodiments, the protein component further comprises lactoferrin.

In some embodiments, the lactoferrin comprises about 4% to about 10%, or about 6% to about 7%, by weight of the protein component. In certain embodiments, the lactoferrin comprises about 6% or about 7% by weight of the protein component.

In certain embodiments, the protein component further comprises one or more digestion-aiding proteins, such as WPH protein, alpha-lactalbumin, or both WPH protein and alpha-lactalbumin.

In some embodiments, the WPH protein comprises about 10% to about 55%, or about 20% to about 50%, by weight of the protein component. In certain embodiments, the WPH protein comprises about 26%, or about 35%, or about 45% by weight of the protein component.

In some embodiments, the alpha-lactalbumin comprises about 5% to about 25%, or about 10% to about 20%, by weight of the protein component. In certain embodiments, the alpha-lactalbumin comprises about 14% or about 18% by weight of the protein component.

In some embodiments, the MFGM is innate or added.

In some embodiments, the fat component further comprises phospholipids, cholesterol, oil, non-hexane extracted DHA, hexane extracted AA, non-hexane extracted AA, or a combination thereof. In certain embodiments, the oil comprises vegetable oil, soy oil, palm oil, or a combination thereof.

In some embodiments, the milk comprises bovine milk. In certain embodiments, the milk comprises whole milk.

In some embodiments, the milk is in an amount to provide about 8% to about 40%, or about 12% to about 30%, by weight of the protein component. In certain embodiments, the milk is in an amount to provide about 16%, or about 18%, or about 25%, by weight of the protein component.

In some embodiments, the formulation comprises a carbohydrate component. In certain embodiments, the carbohydrate component comprises lactose, GOS, FOS, inulin, corn syrup solids, maltodextrin, or a combination thereof.

In some embodiments, the formulation is in powder form.

An aspect of the invention relates to a formulation for oral administration comprising a protein component, a fat component, and a carbohydrate component, in which (a) the protein component comprises whey protein hydrolysate, protein, alpha-lactalbumin, lactoferrin, and osteopontin; (b) the fat component comprises MFGM, phospholipids, cholesterol, non-hexane extracted DHA, and either hexane extracted arachidonic acid or non-hexane extracted AA; and (c) the carbohydrate component comprises lactose and GOS.

A further aspect of the invention relates to a formulation for oral administration comprising a protein component, a fat component, a carbohydrate component, and milk, in which (a) the protein component comprises WPH protein, alpha-lactalbumin, lactoferrin, and osteopontin, such that the WPH protein comprises about 35% by weight of the protein component, the alpha-lactalbumin comprises about 18% by weight of the protein component, the lactoferrin comprises about 6% by weight of the protein component, and the osteopontin comprises about 1% by weight of the protein component; (b) the fat component comprises MFGM, phospholipids, cholesterol, non-hexane extracted DHA, and either hexane extracted AA or non-hexane extracted AA; (c) the carbohydrate component comprises lactose and GOS; and (d) the whole milk is in an amount to provide about 16% by weight of the protein component.

Yet another aspect of the invention relates to a formulation for oral administration comprising a protein component, a fat component, a carbohydrate component, and milk, in which (a) the protein component comprises WPH protein, alpha-lactalbumin, lactoferrin, and osteopontin, such that the partial WPH comprises about 45% by weight of the protein component, the alpha-lactalbumin comprises about 18% by weight of the protein component, the lactoferrin comprises about 6% by weight of the protein component, and the osteopontin comprises about 1% by weight of the protein component; (b) the fat component comprises MFGM, phospholipids, cholesterol, non-hexane extracted DHA, and either hexane extracted AA or non-hexane extracted AA; (c) the carbohydrate component comprises lactose and GOS; and (d) the whole milk is in an amount to provide about 18% by weight of the protein component.

Another aspect of the invention relates to a formulation for oral administration comprising a protein component, a fat component, a carbohydrate component, and milk, in which (a) the protein component comprises WPH protein, alpha-lactalbumin, lactoferrin, and osteopontin, such that the partial WPH comprises about 26% by weight of the protein component, the alpha-lactalbumin comprises about 18% by weight of the protein component, the lactoferrin comprises about 6% by weight of the protein component, and the osteopontin comprises about 1% by weight of the protein component; (b) the fat component comprises MFGM, phospholipids, cholesterol, non-hexane extracted DHA, and either hexane extracted AA or non-hexane extracted AA; (c) the carbohydrate component comprises lactose and GOS; and (d) the whole milk is in an amount to provide about 25% by weight of the protein component.

Moreover, an aspect of the invention relates to a formulation for oral administration comprising a protein component, a fat component, a carbohydrate component, and milk, in which (a) the protein component comprises WPH protein, alpha-lactalbumin, lactoferrin, and osteopontin, such that the partial WPH comprises about 45% by weight of the protein component, the alpha-lactalbumin comprises about 14% by weight of the protein component, the lactoferrin comprises about 7% by weight of the protein component, and the osteopontin comprises about 1% by weight of the protein component; (b) the fat component comprises MFGM, phospholipids, cholesterol, non-hexane extracted DHA, and either hexane extracted AA or non-hexane extracted AA; (c) the carbohydrate component comprises lactose and GOS; and (d) the whole milk is in an amount to provide about 16% by weight of the protein component.

DETAILED DESCRIPTION

The present invention relates to formulations comprising a protein component, in which the protein component comprises one or more digestion-aiding proteins, and/or one or more immunoprotective proteins. These formulations can be used to provide nutritional support to a subject, either as dietary supplements or as a primary source of nutrition. For example, the formulations may be used as a nutritional supplement, children's nutritional product, infant formula, human milk fortifier, growing-up milk or any other nutritional composition designed for an infant or a pediatric subject. In particular embodiments, these formulations may be used as an infant formula.

Combination of Digestion-Aiding Proteins

One aspect of the invention relates to a formulation comprising a protein component, in which the protein component comprises two or more digestion-aiding proteins. A digestion-aiding protein is a protein that is easy to digest and is tolerated by the body. Formulations that are easy to digest are especially important for infants who may be relying on formulas as their primary or sole source of nutrition.

The protein component of a formulation of the present invention may comprise partially hydrolyzed proteins. The hydrolyzed proteins may be treated with enzymes to break down some or most of the proteins that cause adverse symptoms with the goal of reducing allergic reactions, intolerance, and sensitization. The degree of hydrolysis— the extent to which peptide bonds are broken by a hydrolysis method—may be about 3% to about 25%, or about 5% to about 15%. The proteins may be hydrolyzed by any method known in the art. In certain embodiments, the partially hydrolyzed proteins may be whey protein hydrolysate (WPH) protein (N×6.38). WPH protein generally has a size of about 3 to 10 kda, which is small and more easily digested.

The protein component of a formulation of the present invention may comprise proteins that are small in size and are intact, i.e., are not hydrolyzed. For example, the protein component may comprise alpha-lactalbumin-enriched whey protein concentrate or isolate ("alpha-lactalbumin" is used to denote the alpha-lactalbumin protein in the formulation provided by the concentrate or isolate). Alpha-lactalbumin is a small protein (14 kda) that is nearly the size of a hydrolyzed protein. It has been demonstrated to reduce gastrointestinal events and has a high content of essential amino acids, which enables having a lower protein formulation. Further, peptides generated from proteolysis of alpha-lactalbumin have shown in vivo to have bactericidal, opioid agonist, and immunostimulating activity.

The protein component of a formulation of the present invention may comprise other digestion-aiding proteins, including but not limited to, κ-casein, bile salt-stimulated lipase, and amylase.

In embodiments of the invention, the protein component may comprise WPH protein and alpha-lactalbumin. WPH protein and alpha-lactalbumin may be present in the formulation in varying ratios, such as a ratio of about 4:1 to about 1:1 by weight, or a ratio of about 7:2 to about 5:4 by weight.

The amount of WPH protein and alpha-lactalbumin in the protein component may be presented as a percentage of the total amount of protein in the protein component. For example, WPH protein and the alpha-lactalbumin may comprise about 15% to about 80% by weight of the protein component, or about 30% to about 70% by weight of the protein component. In some embodiments, the WPH protein and alpha-lactalbumin may comprise about 40%, or about 44%, or about 49%, or about 53%, or about 59%, or about 63% by weight of the protein component. In certain embodiments, WPH protein and alpha-lactalbumin may comprise 39.5%, 43.8%, 48.6%, 52.9%, or 58.6%, or 62.9% by weight of the protein component.

WPH protein may comprise about 10% to about 55% by weight of the protein component, or about 20% to about 50% by weight of the protein component. In some embodiments, WPH protein may comprise about 26%, or about 35%, or about 45% by weight of the protein component. In certain embodiments, WPH protein may comprise 25.9% or 35% or 45% by weight of the protein component.

Alpha-lactalbumin may comprise about 5% to about 25% by weight of the protein component, or about 10% to about 20% by weight of the protein component. In some embodiments, alpha-lactalbumin may comprise about 14% or about 18% by weight of the protein component. In certain embodiments, alpha-lactalbumin may comprise 13.6% or 17.9% by weight of the protein component.

The amount of WPH protein and alpha-lactalbumin may be presented as grams per liter (g/L) of the formulation in embodiments in which the formulation is in liquid ready-to-feed or as-fed form (see "Methods of Administration" section below). For example, WPH protein and alpha-lactalbumin may comprise about 2 g/L to about 1 g/L, or about 4 g/L to about 15 g/L, of the formulation. In some embodiments, WPH protein and alpha-lactalbumin may comprise about 5 g/L, or about 6 g/L, or about 7 g/L, or about 8 g/L, or about 9 g/L, or about 10 g/L, or about 11 g/L, or about 12 g/L, or about 13 g/L, of the formulation. In certain embodiments, WPH protein and alpha-lactalbumin may comprise 5.4 g/L, 5.9 g/L, 6.6 g/L, 7.1 g/L, or 7.9 g/L, or 8.4 g/L, 8.8 g/L, or 9.7 g/L, 10.8 g/L, 11.7 g/L, or 12.9 g/L, of the formulation. WPH protein may comprise about 1 g/L to about 13 g/L, or about 3 g/L to about 11 g/L, of the formulation. In some embodiments, WPH protein may comprise about 3 g/L, or about 5 g/L, or about 6 g/L, or about 8 g/L, or about 10 g/L, of the formulation. In certain embodiments, WPH protein may comprise 3.5 g/L, 4.7 g/L, or 5.7 g/L, or 6 g/L, or 7.7 g/L, or 9.9 g/L, of the formulation. Alpha-lactalbumin may comprise about 0.5 g/L to about 6 g/L, or about 1 g/L to about 4 g/L, of the formulation. In some embodiments, alpha-lactalbumin may comprise about 2 g/L or about 3 g/L of the formulation. In certain embodiments, alpha-lactalbumin may comprise 2.4 g/L or 3 g/L of the formulation.

The protein component of a formulation of the present invention may comprise proteins in addition to the digestion-aiding proteins described above. For example, the protein component may comprise lactoferrin, osteopontin, β-casein, κ-casein, haptocorrin, lysozyme, secretory IgA, bile-salt stimulated lipase, or a combination thereof. Further additional proteins are disclosed in Bardanzellu et al. ("'Omics' in human colostrum and mature milk: looking to old data with new eyes," *Nutrients*, 2017, vol. 9, no. 8, E843), which is incorporated herein by reference.

The protein component may comprise about 5% to about 20%, or about 8% to about 16%, by weight of the formulation. In some embodiments, the protein component may comprise about 10% or about 15% by weight of the formulation. In certain embodiments, the protein component may comprise 10% or 14.7% by weight of the formulation. Moreover, the protein component may comprise about 5 g/L to about 30 g/L, or about 10 g/L to 25 g/L, of the formulation. In some embodiments, the protein component may comprise about 13 g/L or about 22 g/L of the formulation. In certain embodiments, the protein component may comprise 13.4 g/L or 22 g/L of the formulation.

Combination of Immunoprotective Proteins

Another aspect of the invention relates to a protein component of a formulation comprising two or more immunoprotective proteins. An immunoprotective protein is a protein that promotes the immune system, such as having anti-viral, antibacterial, immunomodulatory and/or anti-inflammatory effects.

The protein component of a formulation of the present invention may comprise lactoferrin. Lactoferrin is an iron-binding glycoprotein that has been proposed to play a role in iron uptake by the intestinal mucosa and to act as a bacteriostatic agent by withholding iron from iron-requiring bacteria. It is also present in neutrophils and is released during inflammation, which suggests that lactoferrin is involved in the immune response. Lactoferrin may function also as a growth factor and/or a bactericidal agent, and may promote maturation of the infant gut.

Lactoferrin may be, for example, isolated from the milk of a non-human animal or produced by a genetically modified organism. The process generally involves an absorbing step to obtain lactoferrin from raw milk material using a weakly acidic cationic exchanger, a washing step to remove non-absorbed substances, and a desorbing step to obtain purified lactoferrin. Varying methods of producing lactoferrin are disclosed in U.S. Pat. Nos. 4,791,193, 5,849,885, 5,861,491, 5,919,913, and 7,368,141, which are all incorporated herein by reference.

The protein component of a formulation of the present invention may comprise osteopontin. Osteopontin is a multifunctional protein present in most tissues and body fluids, with the highest concentrations found in breast milk. It is thought to be involved in cell-mediated immune response, chemotaxis of inflammatory cells, anti-inflammatory responses, induction of T-helper type 1 (Th1)-type immunity, and enhanced host defense against pathogens.

The protein component may comprise other immunoprotective proteins, including but not limited to k-casein, haptocorrin, lysozyme, secretory IgA, lactoperoxidase, and bile-salt stimulated lipase. Additional proteins that relate to immune system processes and that may be included in the protein component are disclosed in Bardanzellu et al., which is incorporated herein by reference.

In embodiments of the invention, the protein component may comprise lactoferrin and osteopontin. Without being bound by theory, it is believed that the effects of lactoferrin and osteopontin may be synergistic, as each protein acts through different mechanisms. Lactoferrin works through iron sequestration to inhibit iron uptake by iron-requiring pathogens, while osteopontin is involved in systemic immunity, working on immune cells themselves and impacting gene expression and cytokines. The systemic immunity combined with a more favorable microbiome could support synergistic immune function. Further, lactoferrin and osteopontin can bind together with high affinity to form a lactoferrin-osteopontin complex, in which multiple cationic lactoferrin molecules bind to one anionic molecule of osteopontin. The characteristics of this complex are not currently known.

Lactoferrin and osteopontin may be present in the formulation in varying ratios, such as a ratio of about 10:1 to about 5:1 by weight, or a ratio of about 9:1 to about 6:1 by weight.

Lactoferrin and osteopontin may comprise about 4% to about 12% by weight of the protein component, or about 6% to about 9% by weight of the protein component of the formulation. In some embodiments, lactoferrin and osteopontin may comprise about 7% to about 8% by weight of the protein component of the formulation. In certain embodiments, lactoferrin and osteopontin may comprise 7.3% or 7.6% by weight of the protein component of the formulation. Lactoferrin may comprise about 4% to about 10% by weight of the protein component, or about 6% to about 7% by weight of the protein component. In some embodiments, lactoferrin may comprise about 6% or about 7% by weight of the protein component. In certain embodiments, lactoferrin may comprise 6.4% or 6.8% by weight of the protein component. Osteopontin may comprise about 0.1% to about 2% by weight of the protein component, or about 0.5% to about 1.5% by weight of the protein component. In some embodiments, osteopontin may comprise about 1% by weight of the protein component. In certain embodiments, osteopontin may comprise 0.77% or 0.98% by weight of the protein component.

In addition, the amount of lactoferrin and osteopontin in the protein component may comprise about 0.4 g/L to about 4 g/L, or about 0.8 g/L to about 3 g/L, of the formulation. In some embodiments, lactoferrin and osteopontin may comprise about 1 g/L or about 2 g/L of the formulation. In certain embodiments, lactoferrin and osteopontin may comprise 0.98 g/L or 1.67 g/L of the formulation. Lactoferrin may comprise about 0.4 g/L to about 3 g/L, or about 0.8 g/L to about 2 g/L, of the formulation. In some embodiments, lactoferrin protein may comprise about 0.9 g/L or about 1.5 g/L of the formulation. In certain embodiments, lactoferrin protein may comprise 0.85 g/L or 1.5 g/L of the formulation. Osteopontin may comprise about 0.05 g/L to about 0.5 g/L, or about 0.08 g/L to about 0.3 g/L, of the formulation. In some embodiments, osteopontin may comprise about 0.1 g/L or about 0.2 g/L of the formulation. In particular embodiments, osteopontin may comprise 0.13 g/L or 0.17 g/L of the formulation.

Notably, in embodiments in which the formulation is applied to infant formulas, the quantities of lactoferrin and osteopontin described herein are not found in typical infant formulas. It is believed that the levels of lactoferrin and osteopontin provide the present formulation with greater immunoprotective properties as compared to infant formulas that are currently on the market. And as further discussed below, in certain embodiments, the formulation contains non-human-derived milk and its components.

The protein component of a formulation of the present invention may comprise proteins in addition to the immunoprotective proteins described above. For example, the protein component may comprise β-casein, κ-casein, haptocorrin, lysozyme, secretory IgA, bile-salt stimulated lipase, or a combination thereof. Additional contemplated proteins are disclosed in Bardanzellu et al., which is incorporated herein by reference.

The protein component may comprise about 5% to about 20%, or about 8% to about 16%, by weight of the formulation. In some embodiments, the protein component may comprise about 10% or about 15% by weight of the formulation. In certain embodiments, the protein component may comprise 10% or 14.7% by weight of the formulation. Moreover, the protein component may comprise about 5 g/L to about 30 g/L, or about 10 g/L to about 25 g/L, of the formulation. In some embodiments, the protein component may comprise about 13 g/L or about 22 g/L of the formulation. In certain embodiments, the protein component may comprise 13.4 g/L or 22 g/L of the formulation.

Combination of Digestion-Aiding Proteins and Immunoprotective Proteins

Yet another aspect of the invention relates to a protein component of the formulation comprising one or more digestion-aiding proteins and one or more immunoprotective proteins. Such a formulation is designed to provide both comfort and immunity, which is in contrast to many known infant formulas that are designed to address either comfort or immunity—not both. For example, infant formulas that focus on providing digestive comfort may comprise 100% hydrolyzed proteins, and therefore lack many of the other types of proteins that infants would otherwise receive through breast milk. On the other hand, infant formulas that focus on providing immunity may comprise only intact proteins and as a result may not be well-tolerated for digestion.

In embodiments of the invention, the protein component of the formulation may comprise WPH protein and lactoferrin. WPH protein and lactoferrin may be present in the formulation in varying ratios, such as a ratio of about 9:1 to about 1:1 by weight, or a ratio of about 8:1 to about 3:1 by weight.

WPH protein and lactoferrin may comprise about 15% to about 65% by weight of the protein component, or about 25% to about 60% by weight of the protein component of the formulation. In some embodiments, WPH protein and lactoferrin may comprise about 32% or about 41% or about 51% by weight of the protein component. In certain embodiments, WPH protein and lactoferrin may comprise 32.4%, or 32.8%, or 41.4%, or 41.8%, or 51.4%, or 51.8%, by weight of the protein component. WPH protein may comprise about 10% to about 55% by weight of the protein component, or about 20% to about 50% by weight of the protein component. In some embodiments, WPH protein may comprise about 26%, or about 35%, or about 45% by weight of the protein component. In certain embodiments, WPH protein may comprise 25.9%, or 35%, or 45% by weight of the protein component. Lactoferrin may comprise about 4% to about 10% by weight of the protein component, or about 6% to about 7% by weight of the protein component. In some embodiments, lactoferrin may comprise about 6% or about 7% by weight of the protein component. In certain embodiments, lactoferrin may comprise 6.4% or 6.8% by weight of the protein component.

Further, the amount of WPH protein and lactoferrin in the protein component of the formulation may comprise about 2 g/L to about 15 g/L, or about 3 g/L to about 14 g/L, of the formulation. In some embodiments, WPH protein and lactoferrin may comprise about 4 g/L, or about 6 g/L, or about 7 g/L, or about 9 g/L, or about 11 g/L, or about 12 g/L, of the formulation. In certain embodiments, WPH protein and lactoferrin may comprise 4.35 g/L, or 5 g/L, or 5.55 g/L, or 6.2 g/L, or 6.55 g/L, or 6.85 g/L, or 8.55 g/L, or 9.2 g/L, or 10.8 g/L, or 11.4 g/L, of the formulation. WPH protein may comprise about 1 g/L to about 13 g/L, or about 3 g/L to about 11 g/L, of the formulation. In some embodiments, WPH protein may comprise about 3 g/L, or about 5 g/L, or about 6 g/L, or about 8 g/L, or about 10 g/L, of the formulation. In certain embodiments, WPH protein may comprise 3.5 g/L, 4.7 g/L, or 5.7 g/L, or 6 g/L, or 7.7 g/L, or 9.9 g/L, of the formulation. Lactoferrin may comprise about 0.4 g/L to about 3 g/L, or about 0.8 g/L to about 2 g/L, of the formulation. In some embodiments, lactoferrin protein may comprise about 0.9 g/L or about 1.5 g/L of the formulation. In certain embodiments, lactoferrin protein may comprise 0.85 g/L or 1.5 g/L of the formulation.

In embodiments of the invention, the protein component of the formulation may comprise WPH protein and osteopontin. WPH protein and osteopontin may be present in the formulation in varying ratios, such as a ratio of about 60:1 to about 10:1 by weight, or a ratio of about 50:1 to about 25:1 by weight.

WPH protein and osteopontin may comprise about 10% to and about 60% by weight of the protein component, or about 20% to about 55% by weight of the protein component of the formulation. In some embodiments, WPH protein and osteopontin may comprise about 27%, or about 36%, or about 46% by weight of the protein component. In certain embodiments, WPH protein and osteopontin may comprise 26.67% or 26.88%, or 35.77%, or 35.98%, or 45.77%, or 45.98% by weight of the protein component. WPH protein may comprise about 10% to about 55% by weight of the protein component, or about 20% to about 50% by weight of the protein component. In some embodiments, WPH protein may comprise about 26%, or about 35%, or about 45% by weight of the protein component. In certain embodiments, WPH protein may comprise 25.9%, or 35%, or 45% by weight of the protein component. Osteopontin may comprise about 0.1% to about 2% by weight of the protein component, or about 0.5% to about 1.5% by weight of the protein component. In some embodiments, osteopontin may comprise about 1% by weight of the protein component. In certain embodiments, osteopontin may comprise 0.77% or 0.98% by weight of the protein component.

In addition, the amount of WPH protein and osteopontin in the formulation may comprise about 1 g/L to about 14 g/L, or about 3 g/L to about 12 g/L, of the formulation. In some embodiments, WPH protein and osteopontin may comprise about 3 g/L, or about 5 g/L, or about 6 g/L, or about 8 g/L, or about 10 g/L, of the formulation. In certain embodiments, WPH protein and osteopontin may comprise 3.63 g/L, or 3.67 g/L, or 4.83 g/L, or 4.87 g/L, or 5.83 g/L, or 5.87 g/L, or 6.13 g/L, or 6.17 g/L, or 7.83 g/L, or 7.87 g/L, or 10.03 g/L, or 10.07 g/L, of the formulation. WPH protein may comprise about 1 g/L to about 13 g/L, or about 3 g/L to about 11 g/L, of the formulation. In some embodiments, WPH protein may comprise about 3 g/L, or about 5 g/L, or about 6 g/L, or about 8 g/L, or about 10 g/L, of the formulation. In certain embodiments, WPH protein may comprise 3.5 g/L, 4.7 g/L, or 5.7 g/L, or 6 g/L, or 7.7 g/L, or 9.9 g/L, of the formulation. Osteopontin may comprise about 0.05 g/L to about 0.5 g/L, or about 0.08 g/L to about 0.3 g/L, of the formulation. In some embodiments, osteopontin may comprise about 0.1 g/L or about 0.2 g/L of the formulation. In particular embodiments, osteopontin may comprise 0.13 g/L or 0.17 g/L of the formulation.

In embodiments of the invention, the protein component of the formulation may comprise alpha-lactalbumin and lactoferrin. Alpha-lactalbumin and lactoferrin may be present in the formulation in varying ratios, such as a ratio of about 4:1 to about 1:1 by weight, or a ratio of about 3:1 to about 2:1 by weight.

Alpha-lactalbumin and lactoferrin may comprise about 9% to about 35% by weight of the protein component, or about 15% to about 30% by weight of the protein component of the formulation. In some embodiments, alpha-lactalbumin and lactoferrin may comprise about 20% or about 25% by weight of the protein component. In certain embodiments, alpha-lactalbumin and lactoferrin may comprise about 20% or about 24.7% by weight of the protein component. Alpha-lactalbumin may comprise about 5% to about 25% by weight of the protein component, or about 10% to about 20% by weight of the protein component. In some embodiments, the alpha-lactalbumin may comprise about 14% or about 18% by weight of the protein component. In certain embodiments, alpha-lactalbumin may comprise 13.6% or 17.9% by weight of the protein component. Lactoferrin may comprise about 4% to about 10% by weight of the protein component, or about 6% to about 7% by weight of the protein component. In some embodiments, lactoferrin may comprise about 6% or about 7% by weight of the protein component. In certain embodiments, lactoferrin may comprise 6.4% or 6.8% by weight of the protein component.

Further, the amount of alpha-lactalbumin and lactoferrin may comprise about 0.9 g/L to about 9 g/L, or about 1 g/L to about 6 g/L, of the formulation. In some embodiments, alpha-lactalbumin and lactoferrin may comprise about 3 g/L or about 5 g/L of the formulation. In certain embodiments, alpha-lactalbumin and lactoferrin may comprise 3.25 g/L or 4.5 g/L of the formulation. Alpha-lactalbumin may comprise about 0.5 g/L to about 6 g/L, or about 1 g/L to about 4 g/L, of the formulation. In some embodiments, alpha-lactalbumin may comprise about 2 g/L or about 3 g/L of the formulation. In certain embodiments, alpha-lactalbumin may comprise 2.4 g/L or 3 g/L of the formulation. Lactoferrin may comprise about 0.4 g/L to about 3 g/L, or about 0.8 g/L to about 2 g/L, of the formulation. In some embodiments, lactoferrin protein may comprise about 0.9 g/L or about 1.5 g/L of the formulation. In certain embodiments, lactoferrin protein may comprise 0.85 g/L or 1.5 g/L of the formulation.

In embodiments of the invention, the protein component of the formulation may comprise alpha-lactalbumin and osteopontin. Alpha-lactalbumin and osteopontin may be present in the formulation in varying ratios, such as a ratio of about 25:1 to about 10:1 by weight, or a ratio of about 20:1 to about 15:1 by weight.

Alpha-lactalbumin and osteopontin may comprise about 5% to about 30% by weight of the protein component, or about 10% to about 25% by weight of the protein component of the formulation. In some embodiments, alpha-lactalbumin and osteopontin may comprise about 14% or about 19% by weight of the protein component. In certain embodiments, alpha-lactalbumin and osteopontin may comprise 14.37% or 18.88% by weight of the protein component. Alpha-lactalbumin may comprise about 5% to about 25% by weight of the protein component, or about 10% to about 20% by weight of the protein component. In some embodiments, the alpha-lactalbumin may comprise about 14% or about 18% by weight of the protein component. In certain embodiments, alpha-lactalbumin may comprise 13.6% or 17.9% by weight of the protein component. Osteopontin may comprise about 0.1% to about 2% by weight of the protein component, or about 0.5% to about 1.5% by weight of the protein component. In some embodiments, osteopontin may comprise about 1% by weight of the protein component. In certain embodiments, osteopontin may comprise 0.77% or 0.98% by weight of the protein component.

Further, the amount of alpha-lactalbumin and osteopontin may comprise about 0.5 g/L to about 7 g/L, or about 1 g/L to about 5 g/L, of the formulation. In some embodiments, alpha-lactalbumin and osteopontin may comprise about 2 g/L or about 3 g/L of the formulation. In certain embodiments, alpha-lactalbumin and osteopontin may comprise 2.53 g/L or 3.17 g/L of the formulation. Alpha-lactalbumin may comprise about 0.5 g/L to about 6 g/L, or about 1 g/L to about 4 g/L, of the formulation. In some embodiments, alpha-lactalbumin may comprise about 2 g/L or about 3 g/L of the formulation. In certain embodiments, alpha-lactalbumin may comprise 2.4 g/L or 3 g/L of the formulation. Osteopontin may comprise about 0.05 g/L to about 0.5 g/L, or about 0.08 g/L to about 0.3 g/L, of the formulation. In certain embodiments, osteopontin may comprise about 0.1 g/L or about 2 g/L of the formulation. In particular embodiments, osteopontin may comprise 0.13 g/L or 0.17 g/L of the formulation.

In addition, the protein component of a formulation of the present invention may comprise a combination of WPH protein, lactoferrin, and osteopontin; or a combination of alpha-lactalbumin, lactoferrin, and osteopontin; or a combination of WPH protein, alpha-lactalbumin, and lactoferrin; or a combination of WPH protein, alpha-lactalbumin, and osteopontin.

In embodiments of the invention, the protein component may comprise WPH protein, alpha-lactalbumin, lactoferrin, and osteopontin. WPH protein, alpha-lactalbumin, lactoferrin, and osteopontin may comprise about 15% to about 95%, or about 45% to about 80%, by weight of the protein component. In certain embodiments, WPH protein, alpha-lactalbumin, lactoferrin, and osteopontin may comprise about 50% to about 75% of the protein component. WPH protein may comprise about 10% to about 55% by weight of the protein component, or about 20% to about 50% by weight of the protein component; alpha-lactalbumin may comprise about 5% to about 25% by weight of the protein component, or about 10% to about 20% by weight of the protein component; lactoferrin may comprise about 4% to about 10% by weight of the protein component, or about 6% to about 7% by weight of the protein component; and osteopontin may comprise about 0.1% to about 2% by weight of the protein component, or about 0.5% to about 1.5% by weight of the protein component. In some embodiments, WPH protein may comprise about 26%, or about 35%, or about 45% by weight of the protein component; alpha-lactalbumin may comprise about 14% or about 18% by weight of the protein component; lactoferrin may comprise about 6% or about 7% by weight of the protein component; and osteopontin may comprise about 1% by weight of the protein component. In certain embodiments, WPH protein may comprise 25.9% or 35% or 45% by weight of the protein component; alpha-lactalbumin may comprise 13.6% or 17.9% by weight of the protein component; lactoferrin may comprise 6.4% or 6.8% by weight of the protein component; and osteopontin may comprise 0.77% or 0.98% by weight of the protein component.

Further, the amount of WPH protein may comprise about 1 g/L to about 13 g/L, or about 3 g/L to about 11 g/L, of the formulation; the amount of alpha-lactalbumin may comprise about 0.5 g/L to about 6 g/L, or about 1 g/L to about 4 g/L, of the formulation; the amount of lactoferrin may comprise about 0.4 g/L to about 3 g/L, or about 0.8 g/L to about 2 g/L, of the formulation; and the amount of osteopontin may comprise about 0.05 g/L to about 0.5 g/L, or about 0.08 g/L to about 0.3 g/L. In some embodiments, WPH protein may comprise about 3 g/L, or about 5 g/L, or about 6 g/L, or about 8 g/L, or about 10 g/L, of the formulation; alpha-lactalbumin may comprise about 2 g/L or about 3 g/L of the formulation; lactoferrin may comprise about 0.9 g/L or about 1.5 g/L of the formulation; and osteopontin may comprise about 0.1 g/L or about 0.2 g/L of the formulation. In certain embodiments, WPH protein may comprise 3.5 g/L, 4.7 g/L, or 5.7 g/L, or 6 g/L, or 7.7 g/L, or 9.9 g/L, of the formulation; alpha-lactalbumin may comprise 2.4 g/L or 3 g/L of the formulation; lactoferrin may comprise 0.85 g/L or 1.5 g/L of the formulation; and osteopontin may comprise about 0.13 g/L or about 0.17 g/L of the formulation.

The protein component of a formulation of the present invention may comprise proteins in addition to the digestion-aiding proteins and immunoprotective proteins described above. Further additional proteins are disclosed in Bardanzellu et al., which is incorporated herein by reference.

The protein component may comprise about 5% to about 20%, or about 8% to about 16%, by weight of the formulation. In some embodiments, the protein component may comprise about 10% or about 15% by weight of the formulation. In certain embodiments, the protein component may comprise 10% or 14.7% by weight of the formulation. Moreover, the protein component may comprise about 5 g/L to about 30 g/L, or about 10 g/L to about 25 g/L, of the formulation. In some embodiments, the protein component may comprise about 13 g/L or about 22 g/L of the formulation. In certain embodiments, the protein component may comprise 13.4 g/L or 22 g/L of the formulation.

Additional Components of the Formulation

In addition to the protein component described above, the formulations of the invention may comprise other components.

For example, the formulations may comprise a fat component. The fat component may comprise, for instance, innate milk fat globule membrane (MFGM), added MFGM, phospholipids, cholesterol, nonhexane-extracted docosahexaenoic acid (DHA), hexane-extracted arachidonic acid (AA), nonhexane-extracted AA, or combination thereof. Suitable fat or lipid sources for the fat component of the formulation may be of any known or used in the art, including but not limited to, animal sources, e.g., milk fat, butter, butter fat, egg yolk lipid, and SN2 palmitate oil; marine sources, such as fish oils, marine oils, single cell oils; vegetable and plant oils, such as corn oil, canola oil, sunflower oil, soybean oil, palm oil, oil, palm olein oil, coconut oil, high oleic sunflower oil, safflower oil, high-oleic safflower oil, evening primrose oil, rapeseed oil, olive oil, flaxseed (linseed) oil, cottonseed oil, high oleic safflower oil, palm stearin oil, palm kernel oil, wheat germ oil; medium chain triglyceride oils and emulsions and esters of fatty acids; and any combinations thereof.

The fat component may comprise about 15% to about 40%, or about 20% to about 35%, by weight of the formulation. In certain embodiments, the fat component may comprise about 28% by weight of the formulation. Moreover, the fat component may comprise about 25 g/L to about 50 g/L, or about 35 g/L to about 40 g/L, of the formulation. In certain embodiments, the fat component may comprise about 37 g/L, including 37.3 g/L, of the formulation.

In certain embodiments, the fat component comprises MFGM. MFGM comprises milk fat globules (MFGs) in a bioactive membrane system, and makes up the fat in bovine milk. Fat is the second largest constituent of bovine milk dry matter having nutritional significance, and MFGM as a whole or some of its associated individual components have physiological and nutritional functions, including supporting antiviral and antibacterial mechanisms that combat gut-derived infections.

In embodiments of the invention, the formulation may comprise osteopontin and MFGM. Such a formulation may be effective in providing immunoprotection, as osteopontin may have a systemic immunity mechanism of action, while MFGM may be acting on mucosal local immunity.

In certain embodiments, the fat component comprises AA. AA may comprise about 0.1% to about 1.2% by weight of the fat component, or about 0.5% to about 0.8% by weight of the fat component. In certain embodiments, AA may comprise about 0.6% of the fat component. In addition, AA may comprise about 0.1 g/L to about 0.2 g/L, or about 0.15 g/L to about 0.18 g/L, of the formulation. In particular embodiments, AA may comprise about 0.17 g/L of the formulation.

In certain embodiments, the fat component comprises DHA. DHA may comprise about 0.05% to about 0.5% by weight of the fat component, or about 0.2% to about 0.4% by weight of the fat component. In certain embodiments, DHA may comprise about 0.3%, or about 0.38%, of the fat component. Further, DHA may comprise about 0.05 g/L to about 0.3 g/L, or about 0.08 g/L to about 0.15 g/L, of the formulation. In particular embodiments, DHA may comprise about 0.11 g/L, or about 0.141 g/L, of the formulation. Moreover, DHA may comprise about 10 mg/100 cal to about 50 mg/100 cal, or about 20 mg/100 cal to about 40 mg/100 cal. In certain embodiments, DHA may comprise about 16 mg/100 cal, or about 20 mg/100 cal, or about 32 mg/100 cal, or about 40 mg/100 cal.

The formulations of the present invention may also comprise a carbohydrate component. The carbohydrate component may comprise, for example, lactose, glucose, fructose, galactooligosaccharide (GOS), fructooligosaccharide (FOS), inulin, corn syrup solids, dextrin, maltodextrin, sucrose, polydextrose, dextrose, tapioca, starch, tapioca starch, rice syrup solids, waxy corn, waxy rice starch, and the like.

The carbohydrate component may comprise about 40% to about 70%, or about 50% to about 60%, by weight of the formulation. In certain embodiments, the carbohydrate component may comprise about 57% by weight of the formulation. Moreover, the carbohydrate component may comprise about 60 g/L to about 90 g/L, or about 70 g/L to about 80 g/L, of the formulation. In certain embodiments, the carbohydrate component may comprise about 76 g/L of the formulation.

In certain embodiments, the formulation may comprise lactose. Lactose is thought to have some important natural prebiotic benefits, and also can provide a natural sweetness to the formulation, which avoids the need for artificial sweeteners.

In some embodiments, the formulation may comprise GOS. GOS is a prebiotic derived from lactose that has been shown to drive stool softening and other potential digestive benefits. GOS may comprise about 2% to about 10% by weight of the carbohydrate component, or about 4% to about 6% by weight of the carbohydrate component. In certain embodiments, GOS may comprise about 5% of the carbohydrate component. In addition, GOS may comprise about 1 g/L to about 8 g/L, or about 3 g/L to about 6 g/L, of the formulation. In particular embodiments, GOS may comprise about 4 g/L of the formulation.

In certain embodiments, the formulation may comprise FOS, which is also a prebiotic.

In embodiments of the invention, the formulation may comprise a milk component. The milk component may comprise milk from a non-human mammal, such as a cow, sheep, goat, yak, water buffalo, horse, reindeer, or camel. The milk may be whole milk, reduced-fat milk (2% milk fat), low-fat milk (1% milk fat), or skimmed milk. In some embodiments, the milk component may comprise non-animal milk, such as soy milk, rice milk, hemp milk, pea milk, or almond or other nut-based milks.

In certain embodiments, the milk component comprises whole milk from a bovine source. Whole milk can help the formulation to attain innate levels of MFGM, phospholipids, and cholesterol that are important, especially for infant development. Whole milk also allows less reliance on other sources of fat, such as oil, to achieve optimal nutrition.

In certain embodiments, the milk in the milk component may also be organic and/or from grass-fed animal sources. Such milk has been linked with higher levels of conjugated linoleic acid and other important vitamins and nutrients, due to the animal spending more time on pasture and consuming higher amounts of grass. Further, organic farming practices reduce exposure to environmental toxins, which are fat soluble and therefore more likely to be found in fat.

In some embodiments, milk may be present in an amount that provide about 8% to about 40%, or about 12% to about 30%, of the protein component. In some embodiments, milk may be present in an amount that provides about 16% or about 18% or about 25% of the protein component. In certain embodiments, milk may be present in an amount that provides 15.7%, 15.9%, 17.7%, or 24.9% of the protein component. One of ordinary skill in the art would understand, based on the protein content of the milk, how much milk is necessary to provide the protein amounts set forth herein.

Finally, the formulation may comprise various vitamins and minerals. The selection of vitamins and minerals and their quantities will vary based on the application of the formulation, as one of ordinary skill in the art would recognize. For example, an infant may have different vitamin and mineral requirements than a child of age one to thirteen years old, or an adult.

Examples of vitamins or derivations thereof may include, but are not limited to, vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, 6-carotene and any combinations thereof.

Examples of minerals or derivations thereof may include, but are not limited to, boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters, and chelates of any mineral compound.

In some embodiments, the vitamins or minerals in the formulation may be provided, in part of or in full, from the milk component. In certain embodiments, the vitamins or minerals in the formulation may be provided from non-milk sources known in the art in addition to, or instead of, from the milk component.

In embodiments in which the formulation of the invention is used in infant formulas, the formulation may comprise a lower amount of iron than typically present in such products. Free iron may feed pathogenic bacteria, foster a less favorable microbiome, and potentially cause digestive discomfort. In addition, babies are born with natural stores of iron that are sufficient until around six months of age, at which point babies typically derive their daily intake of iron from introduction of solid foods and fortified foods.

Typical formulas comprise iron levels of about 1.8 mg/100 cal or 1.9 mg/100 cal, which is greater than ten times the lower limit of the FDA-mandated level of 0.15 mg/100 cal. The formulation of the invention may comprise iron levels no greater than about 1.5 mg/100 cal, or no greater than about 1.3 mg/100 cal. In some embodiments, the formulation of the invention may comprise about 1.1 mg/100 cal.

Dosage Forms

The formulations of the present invention may be in any form suitable for administration including those known in the art, such as a powder, a gel, a suspension, a paste, a solid, a liquid, a liquid concentrate, a reconstituteable powdered milk substitute or a ready-to-use product. For instance, the formulations may be in the form of foods, beverages, tablets, capsules and powders.

In some embodiments, the formulation may be in a form selected from the group consisting of pellets, beads, beadlets, granules, powder, or a combination thereof. In preferred embodiments, the formulation is in powder form, having a particle size in the range of about 2 µm to about 2000 µm, or in the range of about 10 µm to about 500 µm.

In certain embodiments, the formulation may be prepared as a tablet or capsule. These tablets or capsules may contain conventional excipients such as binding agents, fillers, lubricants, disintegrants, or wetting agents. In one aspect the tablets or capsules are coated according to methods well known in the art.

In embodiments in which the formulation is prepared as a tablet, the formulation may be compacted into the dosage form. The disintegrant used in such a tablet is not particularly limited, as far as it is a disintegrant used for pharmaceutical preparations. Examples can include, but are not limited to, one or more of crospovidone, crystalline cellulose, hydroxypropylcellulose with a low degree of substitution, croscarmellose sodium, carmellose calcium, carboxystarch sodium, carboxymethyl starch sodium, potato starch, wheat starch, corn starch, rice starch, partly pregelatinized starch, and hydroxypropyl starch.

Examples of pharmaceutically acceptable additives used in a tablet comprising a formulation of the present invention can include excipients, lubricants, pH adjusters, taste-masking agents, sweeteners, acidifiers, refrigerants, foaming agents, preservatives, fluidizers, antioxidants, colorants, stabilizers, surfactants, buffering agents, flavors, binders and drug solubilizers. A person skilled in the art may immediately list specific examples of these additives.

Examples of a lubricant used in the tablet of the present invention can include light anhydrous silicic acid, magnesium stearate, stearic acid, calcium stearate, aluminum stearate, aluminum monostearate, sucrose fatty acid esters, polyethylene glycol, sodium stearyl fumarate, stearyl alcohol, talc, titanium oxide, hydrous silicon dioxide, magnesium silicate, synthetic aluminum silicate, calcium hydrogen phosphate, hardened castor oil, hardened rapeseed oil, Carnauba Wax, bees wax, microcrystalline wax and sodium lauryl sulfate. One or two or more lubricants can be used.

One or more hydrophilic polymers may be used in a dosage form of the invention. Examples include, but are not limited to, natural or partially or totally synthetic hydrophilic gums such as acacia, gum tragacanth, locust bean gum, guar gum, and karaya gum; cellulose derivatives such as methyl cellulose, hydroxymethyl cellulose, hydroxypropylmethyl cellulose, hydroxypropyl cellulose, hydroxyethyl cellulose, and carboxymethyl cellulose; proteinaceous substances such as agar, pectin, carrageen, and alginates; hydrophilic polymers such as carboxypolymethylene; gelatin; casein; zein; bentonite; magnesium aluminum silicate; polysaccharides; modified starch derivatives; and other hydrophilic polymers known in the art. An addition example is a carbomer, such as Carbopol 971P.

Diluents increase the bulk of a dosage form and may make the dosage form easier to handle. Exemplary diluents include, but are not limited to, lactose, dextrose, saccharose, cellulose, starch, and calcium phosphate for solid dosage forms, e.g., tablets and capsules; olive oil and ethyl oleate for soft capsules; water and vegetable oil for liquid dosage forms, e.g., suspensions and emulsions. Additional suitable diluents include, but are not limited to, sucrose, dextrates, dextrin, maltodextrin, microcrystalline cellulose (e.g., PH102 or PH200, Avicel®), microtine cellulose, powdered cellulose, pregelatinized starch (e.g., Starch 1500®), calcium phosphate dihydrate, soy polysaccharide (e.g., Emcosoy®), gelatin, silicon dioxide, calcium sulfate, calcium carbonate, magnesium carbonate, magnesium oxide, sorbitol, mannitol, kaolin, polymethacrylates (e.g., Eudragit®), potassium chloride, sodium chloride, and talc. One or more diluents may be used in the dosage form.

In embodiments where the formulation is in a solid dosage form, e.g., a tablet, one or more binders can help the ingredients hold together. Binders include, but are not limited to, sugars such as sucrose, lactose, and glucose; corn syrup; soy polysaccharide, gelatin; povidone (e.g., Kollidon®, Plasdone®); Pullulan; cellulose derivatives such as microcrystalline cellulose, hydroxypropylmethyl cellulose (e.g., Methocel®), hydroxypropyl cellulose (e.g., Klucel®), ethylcellulose, hydroxyethyl cellulose, carboxymethylcellulose sodium, and methylcellulose; acrylic and methacrylic acid co-polymers; carbomer (e.g., Carbopol®); polyvinylpolypyrrolidine, polyethylene glycol (Carbowax®); pharmaceutical glaze; alginates such as alginic acid and sodium alginate; gums such as acacia, guar gum, and arabic gums; tragacanth; dextrin and maltodextrin; milk derivatives such as whey; starches such as pregelatinized starch and starch paste; hydrogenated vegetable oil; and magnesium aluminum silicate.

When the formulations are in the form of a tablet, the shape of the tablet is not particularly limited, as far as it can be produced without difficulty using an ordinary manufacturing apparatus or a manufacturing apparatus with some modifications. A disc shape that is a general concept for tablets can be mentioned as a typical example. The whole size is not particularly limited. For example, the shorter diameter (diameter for a disc tablet) is appropriately in the range of about 6 mm to about 20 mm, or about 8 mm to about 12 mm. The thickness is neither particularly limited, but appropriately about 1 mm to about 10 mm, or about 2 mm to about 8 mm.

In various embodiments, the formulations of the present invention may be in a ready-to-use composition. The ready-to-use composition may comprise one or more stabilizing agents, which include, but are not limited to, buffering agents, tonicity agents, polymers, preservatives, antioxidants, sugars and salts, and combinations thereof.

Administration of the Formulation

The present invention is also directed to a method for providing nutritional support to a subject. The method includes administering to the subject an effective amount of a formulation according to the present invention.

The formulation may be administered orally to the subject. In embodiments in which the formulation is in a powder form, the formulation may first be reconstituted with an appropriate amount of water (according to the package directions) to a caloric density of 20-24 cal/oz, depending on the formula type. Alternatively, the formulation may be sprinkled onto foods or added to human breast milk if used as a fortifier.

In some embodiments, the formulation may be expelled directly into a subject's intestinal tract. For example, the formulation may be expelled directly into the gut. In some embodiments, the composition may be administered enterally under the supervision of a physician and may be intended for the specific dietary management of a disease or condition, such as celiac disease and/or food allergy.

In embodiments in which the formulation is an infant formula, the formulation may be delivered to an infant starting at birth. Delivery of the formulation may continue, in some embodiments, through no later than about two years of age; for example, through about one month, or about three months, or about six months, or about nine months, or about one year, or about 15 months, or about 18 months, or about 21 months, about 2 years, or iterations therebetween. In certain embodiments, the infant formula may be administered until the infant has transitioned fully to solid foods, although in some embodiments, the infant formula may continue to be administered as a supplemental source of nutrition.

In embodiments of the invention, the formulation may be administered to infants who were born prematurely. The formulation may be administered until a time that matches full-term gestation. Or, the formulation may be delivered to an infant until at least about three months corrected age, about six months corrected age, about nine months corrected age, about one year corrected age, about 15 months corrected age, about 18 months corrected age, about 21 months corrected age, about two years corrected age, or iterations therebetween. In some embodiments, the formulation may be delivered to a subject as long as is necessary to correct nutritional deficiencies.

In embodiments of the present invention, the formulation may used in a growing-up milk. Growing-up milks are fortified milk-based beverages intended for children over about 1 year of age (generally from about one to about three years of age, or from about four to about six years of age, or from about one year to about six years of age). Growing-up milks can compensate for nutritional deficiencies or can complement a diet to provide additional insurance that a child is receiving all necessary nutrition.

In some embodiments, the formulation may be administered as a daily or multiple-times-a-day supplement.

Preparation of the Formulation

The formulations of the present invention may be prepared by mixing the components of the formulation together. In some embodiments, generally, essential nutrients and other components may be compounded in a wet process and then spray dried, after which certain heat-sensitive ingredients such as vitamins and lactoferrin may be dry-blended into the spray-dried powder. The dried powder product may be packaged and sealed and held until it undergoes a final check for conformance to specifications and regulations, including testing for microbiological contaminants. Liquid ready-to-feed and concentrated liquid infant formula may be processed as a low-acid food and must meet additional processing regulations as well.

The WPH protein may be provided from various sources, such as a commercially available Whey protein hydrolysate that would be Generally Recognized as Safe (GRAS) (the same would be true for all the various ingredients envisioned in this application). For example, in some embodiments, WPH protein may be provided in the formulation using Whey Protein Hydrolysate (DI3071). In certain embodiments WPH protein may be provided in the formulation using Whey Protein Hydrolysate 8350 which is derived from Hilmar Ingredients.

In certain embodiments, the alpha-lactalbumin is provided in the formulation using Lacprodan® ALPHA-10 or ALPHA-20 in the formulation. Both ALPHA-10 and ALPHA-20 are a native whey protein isolate that contains alpha-lactalbumin among other components. ALPHA-10 comprises 43% alpha-lactalbumin, and ALPHA-20 comprises 60% alpha-lactalbumin.

In certain embodiments, lactoferrin is provided in the formulation using Glanbia Nutritionals Inc.'s Bioferrin 2000®. Bioferrin 2000® comprises 93% lactoferrin.

In certain embodiments, osteopontin is provided by including Lacprodan® OPN-10 which comprises 86% osteopontin.

Notably, alpha-lactalbumin, lactoferrin, and osteopontin are also provided in the formulation using whole milk, such as bovine whole milk.

EXAMPLES

This example illustrates different formulations having a protein component that comprises one or more of digestion-aiding WPH protein, digestion-aiding alpha-lactalbumin, immunoprotective lactoferrin, and immunoprotective osteopontin, according to embodiments of the invention. One of ordinary skill in the art would recognize that other digestion-aiding proteins and immunoprotective proteins as described throughout the specification may be substituted into these formulations.

Formulation 1 has a protein component that comprises WPH protein, alpha-lactalbumin, lactoferrin, and osteopontin, in which Lacprodan® ALPHA-10 is the source of the alpha-lactalbumin, in accordance to embodiments of the present invention. The nutrients in this formulation are shown in Table 1 below.

TABLE 1

Nutrients of Formulation 1.

| Nutrient | Quantity (per liter) | Quantity (per 100 g) |
|---|---|---|
| Protein | 13.4 g | 10.0 g |
| Alpha-lactalbumin | 2.4 g | 1.8 g |
| Lactoferrin | 0.85 g | 0.64 g |
| Osteopontin | 130.0 mg | 97.5 mg |
| Fat | 37.3 g | 28.0 g |
| Linoleic Acid | 7308.3 mg | 5481 mg |
| AA | 281 mg | 211 mg |
| DHA | 141 mg | 105.5 mg |
| Carbohydrate | 76.0 g | 57.0 g |
| GOS | 4.0 g | 3.0 g |
| Vitamins - Fat Soluble | | |
| Vitamin A | 2111 IU | 1583 IU |
| Vitamin D | 422 IU | 317 IU |
| Vitamin E | 14.1 IU | 10.6 IU |
| Vitamin K | 63.3 µg | 47.5 µg |
| Vitamins - Water Soluble | | |
| Thiamine (Vitamin $B_1$) | 563 µg | 422 µg |
| Riboflavin | 985 µg | 739 µg |
| Vitamin $B_6$ | 422 µg | 317 µg |
| Vitamin $B_{12}$ | 2.1 µg | 1.6 µg |
| Niacin | 7035 µg | 5276 µg |
| Folic Acid | 113 µg | 84.4 µg |
| Pantothenic Acid | 3518 µg | 2638 µg |
| Biotin | 21.1 µg | 15.8 µg |
| Vitamin C | 84.4 mg | 63.3 mg |
| Choline | 169 mg | 127 mg |
| Inositol | 42.2 mg | 31.7 mg |
| Minerals | | |
| Calcium | 562.8 mg | 422.1 mg |
| Phosphorus | 323.6 mg | 242.7 mg |
| Magnesium | 56.3 mg | 42.2 mg |
| Iron | 7.7 mg | 5.8 mg |
| Zinc | 6.3 mg | 4.7 mg |
| Manganese | 105.5 µg | 79.1 µg |
| Copper | 527.6 µg | 395.7 µg |

TABLE 1-continued

Nutrients of Formulation 1.

| Nutrient | Quantity (per liter) | Quantity (per 100 g) |
|---|---|---|
| Iodine | 105.5 μg | 79.1 μg |
| Selenium | 19.7 μg | 14.8 μg |
| Sodium | 253.3 mg | 190.0 mg |
| Potassium | 759.8 mg | 569.9 mg |
| Chloride | 443.2 mg | 332.4 mg |

For Formulation 1, the different protein sources and their percent contribution to the protein component is shown in Table 2 below.

TABLE 2

Protein sources and their percent contribution in Formulation 1.

| Ingredient | % Ingredient Protein to Total Formula Protein |
|---|---|
| Lacprodan ® DI-3071 (whey protein hydrolysate) | 35.0 |
| Lacprodan ® Alpha-10 whey protein concentrate | 41.8 |
| of which alpha-lactalbumin contributes | 17.9 |
| Bioferrin ® 2000 (lactoferrin) | 6.36 |
| Lacprodan ® OPN-10 (osteopontin) | 0.94 |
| Whole Milk | 15.9 |
| Total | 100.0 |
| Whey-casein ratio | 87.2:12.8 |

Formulation 2 has a protein component that comprises WPH protein, alpha-lactalbumin, lactoferrin, and osteopontin, in which Lacprodan® ALPHA-20 is the source of the alpha-lactalbumin, in accordance to embodiments of the present invention. The nutrients in this formulation are shown in Table 3 below.

TABLE 3

Nutrients of Formulation 2.

| Nutrient | Quantity (per liter) | Quantity (per 100 g) |
|---|---|---|
| Protein | 13.4 g | 10.0 g |
| Alpha-lactalbumin | 2.4 g | 1.8 g |
| Lactoferrin | 0.85 g | 0.64 g |
| Osteopontin | 130.0 mg | 97.5 mg |
| Fat | 37.3 g | 28.0 g |
| Linoleic Acid | 7308.3 mg | 5481 mg |
| AA | 281 mg | 211 mg |
| DHA | 141 mg | 105.5 mg |
| Carbohydrate | 76.0 g | 57.0 g |
| GOS | 4.0 g | 3.0 g |
| Vitamins - Fat Soluble | | |
| Vitamin A | 2111 IU | 1583 IU |
| Vitamin D | 422 IU | 317 IU |
| Vitamin E | 14.1 IU | 10.6 IU |
| Vitamin K | 63.3 μg | 47.5 μg |
| Vitamins - Water Soluble | | |
| Thiamine (Vitamin $B_1$) | 563 μg | 422 μg |
| Riboflavin | 985 μg | 739 μg |
| Vitamin $B_6$ | 422 μg | 317 μg |
| Vitamin $B_{12}$ | 2.1 μg | 1.6 μg |
| Niacin | 7035 μg | 5276 μg |
| Folic Acid | 113 μg | 84.4 μg |
| Pantothenic Acid | 3518 μg | 2638 μg |
| Biotin | 21.1 μg | 15.8 μg |
| Vitamin C | 84.4 mg | 63.3 mg |
| Choline | 169 mg | 127 mg |
| Inositol | 42.2 mg | 31.7 mg |

TABLE 3-continued

Nutrients of Formulation 2.

| Nutrient | Quantity (per liter) | Quantity (per 100 g) |
|---|---|---|
| Minerals | | |
| Calcium | 562.8 mg | 422.1 mg |
| Phosphorus | 323.6 mg | 242.7 mg |
| Magnesium | 56.3 mg | 42.2 mg |
| Iron | 7.7 mg | 5.8 mg |
| Zinc | 6.3 mg | 4.7 mg |
| Manganese | 105.5 μg | 79.1 μg |
| Copper | 527.6 μg | 395.7 μg |
| Iodine | 105.5 μg | 79.1 μg |
| Selenium | 19.7 μg | 14.8 μg |
| Sodium | 253.3 mg | 190.0 mg |
| Potassium | 759.8 mg | 569.9 mg |
| Chloride | 443.2 mg | 332.4 mg |

For Formulation 2, the different protein sources and their percent contribution to the protein component is shown in Table 4 below.

TABLE 4

Protein sources and their percent contribution in Formulation 2.

| Ingredient | % Ingredient Protein to Total Formula Protein |
|---|---|
| Lacprodan ® DI-3071 (whey protein hydrolysate) | 45.0 |
| Lacprodan ® Alpha-20 whey protein concentrate | 29.9 |
| of which alpha-lactalbumin contributes | 17.9 |
| Bioferrin ® 2000 (lactoferrin) | 6.36 |
| Lacprodan ® OPN-10 (osteopontin) | 0.94 |
| Whole Milk | 15.9 |
| Total | 100.0 |
| Whey-casein ratio | 85.8:14.2 |

Formulation 3 has a protein component that comprises WPH protein and alpha-lactalbumin, in which Lacprodan® ALPHA-10 is the source of the alpha-lactalbumin, in accordance to embodiments of the present invention. The nutrients in this formulation are shown in Table 5 below.

TABLE 5

Nutrients of Formulation 3.

| Nutrient | Quantity (per liter) | Quantity (per 100 g) |
|---|---|---|
| Protein | 13.4 g | 10.0 g |
| Alpha-lactalbumin | 2.4 g | 1.8 g |
| Fat | 37.3 g | 28.0 g |
| Linoleic Acid | 7308.3 mg | 5481 mg |
| AA | 281 mg | 211 mg |
| DHA | 141 mg | 105.5 mg |
| Carbohydrate | 76.0 g | 57.0 g |
| GOS | 4.0 g | 3.0 g |
| Vitamins - Fat Soluble | | |
| Vitamin A | 2111 IU | 1583 IU |
| Vitamin D | 422 IU | 317 IU |
| Vitamin E | 14.1 IU | 10.6 IU |
| Vitamin K | 63.3 μg | 47.5 μg |
| Vitamins - Water Soluble | | |
| Thiamine (Vitamin $B_1$) | 563 μg | 422 μg |
| Riboflavin | 985 μg | 739 μg |
| Vitamin $B_6$ | 422 μg | 317 μg |
| Vitamin $B_{12}$ | 2.1 μg | 1.6 μg |
| Niacin | 7035 μg | 5276 μg |
| Folic Acid | 113 μg | 84.4 μg |
| Pantothenic Acid | 3518 μg | 2638 μg |

TABLE 5-continued

Nutrients of Formulation 3.

| Nutrient | Quantity (per liter) | Quantity (per 100 g) |
|---|---|---|
| Biotin | 21.1 μg | 15.8 μg |
| Vitamin C | 84.4 mg | 63.3 mg |
| Choline | 169 mg | 127 mg |
| Inositol | 42.2 mg | 31.7 mg |
| Minerals | | |
| Calcium | 562.8 mg | 422.1 mg |
| Phosphorus | 323.6 mg | 242.7 mg |
| Magnesium | 56.3 mg | 42.2 mg |
| Iron | 7.7 mg | 5.8 mg |
| Zinc | 6.3 mg | 4.7 mg |
| Manganese | 105.5 μg | 79.1 μg |
| Copper | 527.6 μg | 395.7 μg |
| Iodine | 105.5 μg | 79.1 μg |
| Selenium | 19.7 μg | 14.8 μg |
| Sodium | 253.3 mg | 190.0 mg |
| Potassium | 759.8 mg | 569.9 mg |
| Chloride | 443.2 mg | 332.4 mg |

For Formulation 3, the different protein sources and their percent contribution to the protein component is shown in Table 6 below.

TABLE 6

Protein sources and their percent contribution in Formulation 3.

| Ingredient | % Ingredient Protein to Total Formula Protein |
|---|---|
| Lacprodan ® DI-3071 (whey protein hydrolysate) | 35.0 |
| Lacprodan ® Alpha-10 whey protein concentrate | 41.8 |
| of which alpha-lactalbumin contributes | 17.9 |
| Whole Milk | 23.2 |
| Total | 100.0 |
| Whey-casein ratio | 81.4:18.6 |

Formulation 4 has a protein component that comprises lactoferrin and osteopontin, in accordance to embodiments of the present invention. The nutrients in this formulation are shown in Table 7 below.

TABLE 7

Nutrients of Formulation 4.

| Nutrient | Quantity (per liter) | Quantity (per 100 g) |
|---|---|---|
| Protein | 13.4 g | 10.0 g |
| Lactoferrin | 0.85 g | 0.64 g |
| Osteopontin | 130.0 mg | 97.5 mg |
| Fat | 37.3 g | 28.0 g |
| Linoleic Acid | 7308.3 mg | 5481 mg |
| AA | 281 mg | 211 mg |
| DHA | 141 mg | 105.5 mg |
| Carbohydrate | 76.0 g | 57.0 g |
| GOS | 4.0 g | 3.0 g |
| Vitamins - Fat Soluble | | |
| Vitamin A | 2111 IU | 1583 IU |
| Vitamin D | 422 IU | 317 IU |
| Vitamin E | 14.1 IU | 10.6 IU |
| Vitamin K | 63.3 μg | 47.5 μg |
| Vitamins - Water Soluble | | |
| Thiamine (Vitamin $B_1$) | 563 μg | 422 μg |
| Riboflavin | 985 μg | 739 μg |
| Vitamin $B_6$ | 422 μg | 317 μg |
| Vitamin $B_{12}$ | 2.1 μg | 1.6 μg |
| Niacin | 7035 μg | 5276 μg |
| Folic Acid | 113 μg | 84.4 μg |
| Pantothenic Acid | 3518 μg | 2638 μg |
| Biotin | 21.1 μg | 15.8 μg |
| Vitamin C | 84.4 mg | 63.3 mg |
| Choline | 169 mg | 127 mg |
| Inositol | 42.2 mg | 31.7 mg |
| Minerals | | |
| Calcium | 562.8 mg | 422.1 mg |
| Phosphorus | 323.6 mg | 242.7 mg |
| Magnesium | 56.3 mg | 42.2 mg |
| Iron | 7.7 mg | 5.8 mg |
| Zinc | 6.3 mg | 4.7 mg |
| Manganese | 105.5 μg | 79.1 μg |
| Copper | 527.6 μg | 395.7 μg |
| Iodine | 105.5 μg | 79.1 μg |
| Selenium | 19.7 μg | 14.8 μg |
| Sodium | 253.3 mg | 190.0 mg |
| Potassium | 759.8 mg | 569.9 mg |
| Chloride | 443.2 mg | 332.4 mg |

For Formulation 4, the different protein sources and their percent contribution to the protein component is shown in Table 8 below.

TABLE 8

Protein sources and their percent contribution in Formulation 4.

| Ingredient | % Ingredient Protein to Total Formula Protein |
|---|---|
| Whey protein concentrate-35 | 70.0 |
| Bioferrin ® 2000 (lactoferrin) | 6.4 |
| Lacprodan ® OPN-10 (osteopontin) | 0.94 |
| Whole Milk | 22.7 |
| Total | 100.0 |
| Whey-casein ratio | 81.8:18.2 |

Formulation 5 has a protein component that comprises osteopontin, in accordance to embodiments of the present invention. The nutrients in this formulation are shown in Table 9 below.

TABLE 9

Nutrients of Formulation 5.

| Nutrient | Quantity (per liter) | Quantity (per 100 g) |
|---|---|---|
| Protein | 13.4 g | 10.0 g |
| Osteopontin | 130.0 mg | 97.5 mg |
| Fat | 37.3 g | 28.0 g |
| Linoleic Acid | 7308.3 mg | 5481 mg |
| AA | 281 mg | 211 mg |
| DHA | 141 mg | 105.5 mg |
| Carbohydrate | 76.0 g | 57.0 g |
| GOS | 4.0 g | 3.0 g |
| Vitamins - Fat Soluble | | |
| Vitamin A | 2111 IU | 1583 IU |
| Vitamin D | 422 IU | 317 IU |
| Vitamin E | 14.1 IU | 10.6 IU |
| Vitamin K | 63.3 μg | 47.5 μg |
| Vitamins - Water Soluble | | |
| Thiamine (Vitamin $B_1$) | 563 μg | 422 μg |
| Riboflavin | 985 μg | 739 μg |
| Vitamin $B_6$ | 422 μg | 317 μg |
| Vitamin $B_{12}$ | 2.1 μg | 1.6 μg |

TABLE 9-continued

Nutrients of Formulation 5.

| Nutrient | Quantity (per liter) | Quantity (per 100 g) |
|---|---|---|
| Niacin | 7035 μg | 5276 μg |
| Folic Acid | 113 μg | 84.4 μg |
| Pantothenic Acid | 3518 μg | 2638 μg |
| Biotin | 21.1 μg | 15.8 μg |
| Vitamin C | 84.4 mg | 63.3 mg |
| Choline | 169 mg | 127 mg |
| Inositol | 42.2 mg | 31.7 mg |
| Minerals | | |
| Calcium | 562.8 mg | 422.1 mg |
| Phosphorus | 323.6 mg | 242.7 mg |
| Magnesium | 56.3 mg | 42.2 mg |
| Iron | 7.7 mg | 5.8 mg |
| Zinc | 6.3 mg | 4.7 mg |
| Manganese | 105.5 μg | 79.1 μg |
| Copper | 527.6 μg | 395.7 μg |
| Iodine | 105.5 μg | 79.1 μg |
| Selenium | 19.7 μg | 14.8 μg |
| Sodium | 253.3 mg | 190.0 mg |
| Potassium | 759.8 mg | 569.9 mg |
| Chloride | 443.2 mg | 332.4 mg |

For Formulation 5, the different protein sources and their percent contribution to the protein component is shown in Table 10 below.

TABLE 10

Protein sources and their percent contribution in Formulation 5.

| Ingredient | % Ingredient Protein to Total Formula Protein |
|---|---|
| Whey protein concentrate-35 | 80.0 |
| Lacprodan ® OPN-10 (osteopontin) | 0.94 |
| Whole Milk | 19.1 |
| Total | 100.0 |
| Whey-casein ratio | 84.8:15.2 |

Formulation 6 has a protein component that comprises alpha-lactalbumin and osteopontin, in accordance to embodiments of the present invention. The nutrients in this formulation are shown in Table 11 below.

TABLE 11

Nutrients of Formulation 6.

| Nutrient | Quantity (per liter) | Quantity (per 100 g) |
|---|---|---|
| Protein | 13.4 g | 10.0 g |
| Alpha-lactalbumin | 2.4 g | 1.8 g |
| Osteopontin | 130.0 mg | 97.5 mg |
| Fat | 37.3 g | 28.0 g |
| Linoleic Acid | 7308.3 mg | 5481 mg |
| AA | 281 mg | 211 mg |
| DHA | 141 mg | 105.5 mg |
| Carbohydrate | 76.0 g | 57.0 g |
| GOS | 4.0 g | 3.0 g |
| Vitamins - Fat Soluble | | |
| Vitamin A | 2111 IU | 1583 IU |
| Vitamin D | 422 IU | 317 IU |
| Vitamin E | 14.1 IU | 10.6 IU |
| Vitamin K | 63.3 μg | 47.5 μg |
| Vitamins - Water Soluble | | |
| Thiamine (Vitamin $B_1$) | 563 μg | 422 μg |
| Riboflavin | 985 μg | 739 μg |
| Vitamin $B_6$ | 422 μg | 317 μg |

TABLE 11-continued

Nutrients of Formulation 6.

| Nutrient | Quantity (per liter) | Quantity (per 100 g) |
|---|---|---|
| Vitamin $B_{12}$ | 2.1 μg | 1.6 μg |
| Niacin | 7035 μg | 5276 μg |
| Folic Acid | 113 μg | 84.4 μg |
| Pantothenic Acid | 3518 μg | 2638 μg |
| Biotin | 21.1 μg | 15.8 μg |
| Vitamin C | 84.4 mg | 63.3 mg |
| Choline | 169 mg | 127 mg |
| Inositol | 42.2 mg | 31.7 mg |
| Minerals | | |
| Calcium | 562.8 mg | 422.1 mg |
| Phosphorus | 323.6 mg | 242.7 mg |
| Magnesium | 56.3 mg | 42.2 mg |
| Iron | 7.7 mg | 5.8 mg |
| Zinc | 6.3 mg | 4.7 mg |
| Manganese | 105.5 μg | 79.1 μg |
| Copper | 527.6 μg | 395.7 μg |
| Iodine | 105.5 μg | 79.1 μg |
| Selenium | 19.7 μg | 14.8 μg |
| Sodium | 253.3 mg | 190.0 mg |
| Potassium | 759.8 mg | 569.9 mg |
| Chloride | 443.2 mg | 332.4 mg |

For Formulation 6, the different protein sources and their percent contribution to the protein component is shown in Table 12 below.

TABLE 12

Protein sources and their percent contribution in Formulation 6.

| Ingredient | % Ingredient Protein to Total Formula Protein |
|---|---|
| Whey protein concentrate-35 | 38.0 |
| Lacprodan ® Alpha-10 whey protein concentrate | 41.8 |
| of which alpha-lactalbumin contributes | 17.9 |
| Lacprodan ® OPN-10 (osteopontin) | 0.94 |
| Whole Milk | 19.3 |
| Total | 100.0 |
| Whey-casein ratio | 84.6:15.4 |

For Formulation 7, the different protein sources and their percent contribution to the protein component is shown in Table 12 below.

TABLE 13

Protein sources and their percent contribution in Formulation 7.

| Ingredient | % Ingredient Protein to Total Formula Protein |
|---|---|
| Lacprodan ® DI-3071 (whey protein hydrolysate) | 26.0 |
| Lacprodan ® Alpha-10 whey protein concentrate | 41.8 |
| of which alpha-lactalbumin contributes | 17.9 |
| Bioferrin ® 2000 (lactoferrin) | 6.36 |
| Lacprodan ® OPN-10 (osteopontin) | 0.94 |
| Whole Milk | 24.9 |
| Total | 100.0 |
| Whey-casein ratio | 80:20 |

The foregoing description is given for clearness of understanding only, and no unnecessary limitations should be understood therefrom, as modifications within the scope of the invention may be apparent to those having ordinary skill in the art.

Throughout this specification and the claims that follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed:

1. A formulation for oral administration comprising a protein component, the protein component designating the entire amount of protein comprised by the formulation, wherein the protein component comprises:
   (a) one or more digestion-aiding proteins, comprising whey protein hydrolysate (WPH), and alpha-lactalbumin; and
   (b) one or more immunoprotective proteins, comprising lactoferrin;
   wherein the one or more digestion-aiding proteins and the one or more immunoprotective proteins comprise about 15% to about 75% by weight of the protein component;
   wherein the WPH comprises 26% to 35% by weight of the protein component;
   wherein the alpha-lactalbumin comprises 14% to 20% by weight of the protein component;
   wherein the lactoferrin comprises 1% to 6% by weight of the protein component;
   wherein the formulation comprises a milk component comprising whole cow's milk;
   wherein the milk component comprises milk protein naturally occurring in the whole cow's milk, the entire amount of the milk protein being considered part of the protein component; and
   wherein the whole cow's milk is in an amount to provide 25% to 30% by weight of the protein component.

2. A formulation for oral administration comprising a protein component, a fat component, a carbohydrate component, and whole milk, wherein:
   (a) the protein component, designating the entire amount of protein comprised by the formulation, including protein naturally occurring in the milk, comprises whey protein hydrolysate (WPH), alpha-lactalbumin, and lactoferrin, wherein the WPH comprises 26% to 35% by weight of the protein component, the alpha-lactalbumin comprises 14% to 20% by weight of the protein component, and the lactoferrin comprises 1% to 6% by weight of the protein component;
   (b) the fat component comprises one or more vegetable oils, one or more plant oils, or a combination thereof;
   (c) the carbohydrate component comprises lactose and galactooligosaccharide; and
   (d) the whole milk is in an amount to provide 25% to 30% by weight of the protein component.

3. The formulation of claim 2, wherein:
   the WPH comprises 26% to 28% of the protein component; and
   the alpha-lactalbumin comprises 18% to 20% of the protein component.

4. The formulation of claim 2, wherein:
   the WPH and the lactoferrin are present in the formulation in a ratio of 3:1 to 7:1 by weight; and
   the alpha-lactalbumin and the lactoferrin are present in the formulation in a ratio of 2:1 to 4:1 by weight.

* * * * *